(12) United States Patent
Renga et al.

(10) Patent No.: US 9,045,427 B2
(45) Date of Patent: Jun. 2, 2015

(54) FLUOROPICOLINOYL FLUORIDES AND PROCESSES FOR THEIR PREPARATION

(71) Applicant: Dow AgroSciences LLC, Indianapolis, IN (US)

(72) Inventors: James M. Renga, Indianapolis, IN (US); Yang Cheng, Midland, MI (US); Joseck M. Muhuhi, Midland, MI (US); David E. Podhorez, Midland, MI (US); Gary A. Roth, Midland, MI (US); Scott P. West, Midland, MI (US); Gregory T. Whiteker, Carmel, IN (US); Yuanming Zhu, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 13/949,053

(22) Filed: Jul. 23, 2013

(65) Prior Publication Data

US 2014/0031558 A1     Jan. 30, 2014

Related U.S. Application Data

(60) Provisional application No. 61/675,229, filed on Jul. 24, 2012.

(51) Int. Cl.
    *C07D 213/78*     (2006.01)
    *C07D 213/803*     (2006.01)
    *C07D 213/807*     (2006.01)

(52) U.S. Cl.
CPC .......... *C07D 213/78* (2013.01); *C07D 213/807* (2013.01); *C07D 213/803* (2013.01)

(58) Field of Classification Search
None
See application file for complete search history.

(56) References Cited

U.S. PATENT DOCUMENTS

| 4,847,442 | A | 7/1989 | Nalelwajek et al. |
| 6,297,197 | B1 | 10/2001 | Fields et al. |
| 6,784,137 | B2 | 8/2004 | Balko et al. |
| 7,314,849 | B2 | 1/2008 | Balko et al. |
| 7,432,227 | B2 | 10/2008 | Balko et al. |
| 2001/0047099 | A1 | 11/2001 | Fields et al. |
| 2012/0190859 | A1 | 7/2012 | Zhu et al. |
| 2012/0190860 | A1 | 7/2012 | Whiteker et al. |

FOREIGN PATENT DOCUMENTS

| EP | 1 500 641 | | 1/2005 |
| JP | 62181257 A | * | 8/1987 |

OTHER PUBLICATIONS

Translation of JP 62181257, Asahi Chemical Industry, Aug. 1987.*
Baumann et al., "The Use of Diethylaminosulfur Trifluoride (DAST) for Fluorination in a Continuous-Flow Microreactor," Synlett., 2008(14):2111-2114 (2008).
Pittelkow et al., "TFFH as an Excellent Reagent for Acylation of Alcohols, Thiols and Dithiocarbamates," Synthesis, 15(29):2485-2492 (2004).

* cited by examiner

*Primary Examiner* — Zinna Northington Davis
(74) *Attorney, Agent, or Firm* — Michael R. Asam; Meunier Carlin & Curfman, LLC

(57) ABSTRACT

Provided herein are fluoropicolinoyl fluorides and processes for their preparation. In some embodiments, provided herein is a process for the preparation of 5-fluoro-6-aryl-picolinoyl fluorides from chloropicolinoyl chlorides.

22 Claims, No Drawings

FLUOROPICOLINOYL FLUORIDES AND PROCESSES FOR THEIR PREPARATION

1. CLAIM OF PRIORITY

Priority is claimed herein to U.S. Provisional Application No. 61/675,229 entitled "Fluoropicolinoyl Fluorides and Processes for their Preparation," filed Jul. 24, 2012. The above-referenced application is incorporated by reference herein in its entirety.

2. FIELD

Provided herein are fluoropicolinoyl fluorides and processes for their preparation. In some embodiments, provided herein is a process for the preparation of 5-fluoro-6-aryl-picolinoyl fluorides from chloropicolinoyl chlorides.

3. BACKGROUND

U.S. Pat. No. 6,297,197 B1 describes inter alia certain 6-(alkoxy or aryloxy)-4-amino-3-chloro-5-fluoropicolinate compounds and their use as herbicides. U.S. Pat. Nos. 6,784,137 B2 and 7,314,849 B2 describe inter alia certain 6-(aryl)-4-amino-3-chloro-5-fluoropicolinate compounds and their use as herbicides. U.S. Pat. No. 7,432,227 B2 describes inter alia certain 6-(alkyl)-4-amino-3-chloro-5-fluoropicolinate compounds and their use as herbicides. Each of these patents describes the manufacture of 4-amino-3-chloro-5-fluoropicolinate starting materials by fluorination of the corresponding 5-unsubstituted pyridines with 1-(chloromethyl)-4-fluoro-1,4-diazoniabicyclo[2.2.2]octane bis(tetrafluoroborate). It would be advantageous to provide more direct and efficient methods for the preparation of 4-amino-5-fluoro-3-halo-6-(substituted)picolinates and related compounds, e.g., by the use of reagents and/or chemical intermediates which provide improve time and cost efficiency.

4. SUMMARY OF THE DISCLOSURE

Provided herein are fluoropicolinoyl fluorides and processes for their preparation. In one embodiment, provided herein is a process for the preparation of a compound of the Formula I:

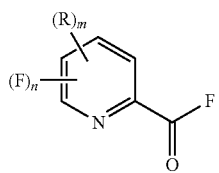

(I)

wherein

R is selected from the group consisting of halo; alkyl; cycloalkyl; alkenyl; alkynyl; alkoxy and aryl substituted with from 0 to 5 substituents independently selected from halo, $C_1$-$C_4$ alkyl, $C_1$-$C_4$ haloalkyl, $C_1$-$C_4$ alkoxy and $C_1$-$C_4$ haloalkoxy;

m is 0, 1, 2 or 3; and n is 1, 2, 3 or 4;

wherein the sum of m and n is less than or equal to 4;

which comprises fluorinating a compound of Formula A:

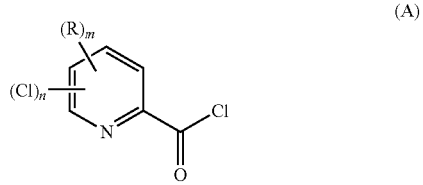

(A)

wherein R, m and n are as previously defined;

with a source of fluoride ion to produce the compound of the Formula I.

Fluoropicolinoyl fluorides provided herein may be prepared from chloropicolinoyl chlorides as shown in Scheme 1 below.

Scheme 1

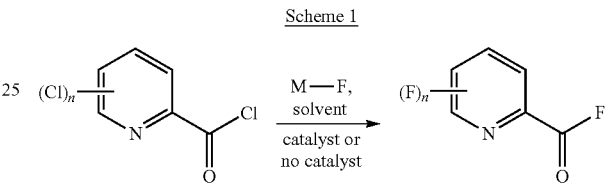

n = 1 to 4

In Scheme 1, "M-F" represents a metal fluoride salt, including but not limited to, sodium fluoride, potassium fluoride or cesium fluoride. In certain embodiments, the solvent is sulfolane or acetonitrile.

In other embodiments, provided herein is a process for the preparation of fluoro-6-aryl-picolinoyl fluorides from chloro-6-aryl-picolinoyl acid chlorides as shown in Scheme 2 below.

Scheme 2

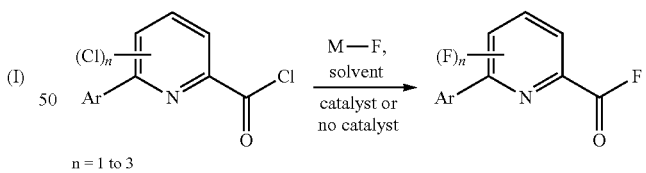

n = 1 to 3

In Scheme 2, "M-F" represents a metal fluoride salt, including but not limited to, sodium fluoride, potassium fluoride or cesium fluoride. In certain embodiments, the solvent is sulfolane or acetonitrile. "Ar" represents an aryl group.

5. DETAILED DESCRIPTION

Provided herein are fluoropicolinoyl fluorides and processes for their preparation. In one embodiment, provided herein is a process for the preparation of a compound of the Formula I:

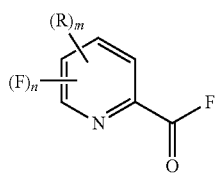

wherein
R is selected from the group consisting of halo; alkyl; cycloalkyl; alkenyl; alkynyl; alkoxy and aryl substituted with from 0 to 5 substituents independently selected from halo, $C_1$-$C_4$ alkyl, $C_1$-$C_4$ haloalkyl, $C_1$-$C_4$ alkoxy and $C_1$-$C_4$ haloalkoxy;
m is 0, 1, 2 or 3; and
n is 1, 2, 3 or 4;
wherein the sum of m and n is less than or equal to 4;
which comprises fluorinating a compound of Formula A:

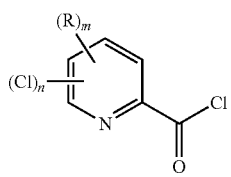

wherein R, m and n are as previously defined;
with a source of fluoride ion to produce the compound of the Formula I.

In some embodiments, provided herein is a process for the preparation of a compound of the Formula I, wherein m is 0. In other embodiments, m is 1.

In some embodiments, provided herein is a process for the preparation of a compound of the Formula I, wherein n is 1, 2 or 3. In some embodiments, n is 2 or 3. In other embodiments, n is 2. In other embodiments, n is 3.

In some embodiments, the compound of Formula I is:

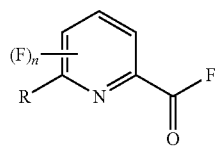

wherein R is aryl substituted with from 0 to 5 substituents independently selected from halo, $C_1$-$C_4$ alkyl, $C_1$-$C_4$ haloalkyl, $C_1$-$C_4$ alkoxy and $C_1$-$C_4$ haloalkoxy; and
n is 1, 2 or 3.

In some embodiments, the compound of Formula I is:

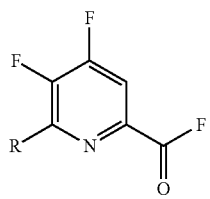

wherein R is phenyl substituted with from 0 to 5 substituents independently selected from halo, $C_1$-$C_4$ alkyl, $C_1$-$C_4$ haloalkyl, $C_1$-$C_4$ alkoxy and $C_1$-$C_4$ haloalkoxy.

In some embodiments, the process includes a catalyst selected from a crown ether, a phosphonium halide, a polyether, a phosphazenium salt, and a tetra-substituted ammonium halide. In certain embodiments, the catalyst is a crown ether. In one embodiment, the crown ether is 18-crown-6.

In some embodiments, the source of fluoride ion is a metal fluoride. In some embodiments, the metal fluoride is selected from sodium fluoride, potassium fluoride and cesium fluoride. In one embodiment, the metal fluoride is potassium fluoride.

In some embodiments, the process includes a solvent. In some embodiments, the solvent is selected from an alkyl nitrile or an alkyl sulfone. In certain embodiments, the solvent is acetonitrile or sulfolane.

In one embodiment, provided herein is a process for the preparation of a compound of the formula:

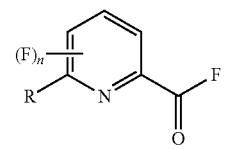

wherein
R is phenyl substituted with from 0 to 5 substituents independently selected from halo, $C_1$-$C_4$ alkyl, $C_1$-$C_4$ haloalkyl, $C_1$-$C_4$ alkoxy and $C_1$-$C_4$ haloalkoxy; and
n is 1 or 2;
which comprises reacting a compound of Formula A:

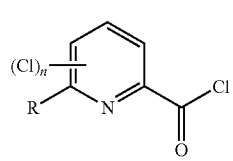

wherein R is phenyl substituted with from 0 to 5 substituents independently selected from halo, $C_1$-$C_4$ alkyl, $C_1$-$C_4$ haloalkyl, $C_1$-$C_4$ alkoxy and $C_1$-$C_4$ haloalkoxy; and
n is 1 or 2;
with potassium fluoride in the presence of a crown ether and a solvent.

In one embodiment, the solvent is acetonitrile or sulfolane.

Also provided herein is a compound of the Formula I:

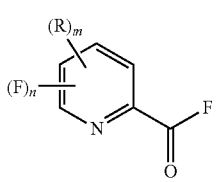

wherein
R is selected from the group consisting of halo; alkyl; cycloalkyl; alkenyl; alkynyl; alkoxy and aryl substituted with from 0 to 5 substituents independently selected from halo, $C_1$-$C_4$ alkyl, $C_1$-$C_4$ haloalkyl, $C_1$-$C_4$ alkoxy and $C_1$-$C_4$ haloalkoxy;
m is 0, 1, 2 or 3; and
n is 0, 1, 2, 3 or 4;
wherein the sum of m and n is between 1 and 4.

In one embodiment, m is 0 and n is 1, 2, 3 or 4.

In another embodiment, the compound is of the formula:

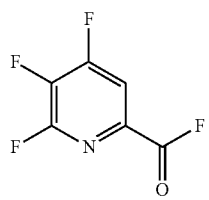 [SMILES: O=C(F)c1cc(F)c(F)c(F)n1]

In another embodiment, the compound is of the formula:

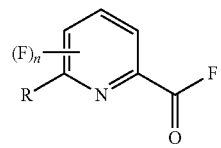

wherein R is aryl substituted with from 0 to 5 substituents independently selected from halogen, $C_1$-$C_4$ alkyl, $C_1$-$C_4$ haloalkyl, $C_1$-$C_4$ alkoxy and $C_1$-$C_4$ haloalkoxy; and
n is 1, 2 or 3. In one embodiment, n is 1 or 2.

In another embodiment, the compound is of the formula:

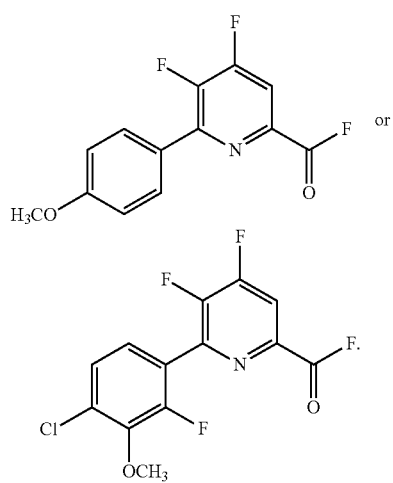

In another embodiment, provided herein is a process for the preparation of a compound of the Formula II:

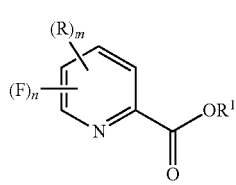

wherein
R is selected from the group consisting of halo; alkyl; cycloalkyl; alkenyl; alkynyl; alkoxy and aryl substituted with from 0 to 5 substituents independently selected from halo, $C_1$-$C_4$ alkyl, $C_1$-$C_4$ haloalkyl, $C_1$-$C_4$ alkoxy and $C_1$-$C_4$ haloalkoxy;
$R^1$ is selected from the group consisting of H; alkyl; cycloalkyl; alkenyl; alkynyl; and aryl substituted with from 0 to 5 substituents independently selected from halo, $C_1$-$C_4$ alkyl, $C_1$-$C_4$ haloalkyl, $C_1$-$C_4$ alkoxy and $C_1$-$C_4$ haloalkoxy;
m is 0, 1, 2 or 3; and
n is 0, 1, 2, 3 or 4;
wherein the sum of m and n is between 1 and 4;
which comprises (a) fluorinating a compound of Formula A:

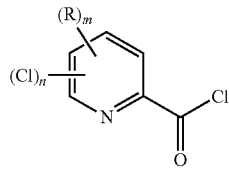

with a source of fluoride ion to produce a compound of the Formula I:

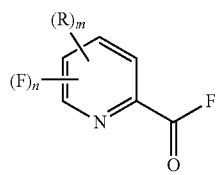

wherein R is selected from the group consisting of halo; alkyl; cycloalkyl; alkenyl; alkynyl; alkoxy and aryl substituted with from 0 to 5 substituents independently selected from halo, $C_1$-$C_4$ alkyl, $C_1$-$C_4$ haloalkyl, $C_1$-$C_4$ alkoxy and $C_1$-$C_4$ haloalkoxy;
m is 0, 1, 2 or 3; and
n is 0, 1, 2, 3 or 4;
which further comprises (b) reacting a compound for Formula I with a source of $R^1$OH to produce a compound of Formula II.

In another embodiment, provided herein is a process for the preparation of a compound of the Formula II:

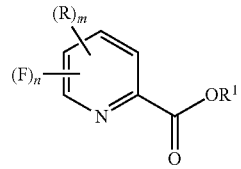

wherein
R is selected from the group consisting of halo; alkyl; cycloalkyl; alkenyl; alkynyl; alkoxy and aryl substituted with from 0 to 5 substituents independently selected from halo, $C_1$-$C_4$ alkyl, $C_1$-$C_4$ haloalkyl, $C_1$-$C_4$ alkoxy and $C_1$-$C_4$ haloalkoxy;

$R^1$ is selected from the group consisting of H; alkyl; cycloalkyl; alkenyl; alkynyl; unsubstituted or substituted $C_7$-$C_{11}$ arylalkyl; and aryl substituted with from 0 to 5 substituents independently selected from halo, $C_1$-$C_4$ alkyl, $C_1$-$C_4$ haloalkyl, $C_1$-$C_4$ alkoxy and $C_1$-$C_4$ haloalkoxy;

m is 0, 1, 2 or 3; and n is 0, 1, 2, 3 or 4;

wherein the sum of m and n is between 1 and 4;

which comprises (a) fluorinating a compound of Formula A:

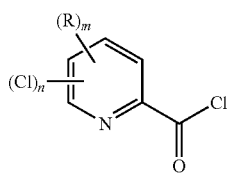

(A)

with a source of fluoride ion to produce a compound of the Formula I:

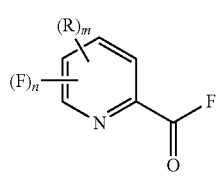

(I)

wherein R is selected from the group consisting of halo; alkyl; cycloalkyl; alkenyl; alkynyl; alkoxy and aryl substituted with from 0 to 5 substituents independently selected from halo, $C_1$-$C_4$ alkyl, $C_1$-$C_4$ haloalkyl, $C_1$-$C_4$ alkoxy and $C_1$-$C_4$ haloalkoxy;

m is 0, 1, 2 or 3; and n is 0, 1, 2, 3 or 4;

which further comprises (b) reacting a compound for Formula I with a source of $R^1OH$ to produce a compound of Formula II.

In some embodiments, the reaction of step (b) further comprises a base. In some embodiments, the base is a trialkyl amine base, e.g., triethylamine.

Fluoropicolinoyl fluorides provided herein may be prepared from chloropicolinoyl chlorides as shown in Scheme 1 below.

Scheme 1

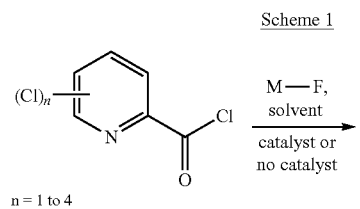

In Scheme 1, "M-F" represents a metal fluoride salt, including but not limited to, sodium fluoride, potassium fluoride or cesium fluoride. In certain embodiments, the solvent is sulfolane or acetonitrile.

In other embodiments, provided herein is a process for the preparation of fluoro-6-aryl-picolinoyl fluorides from chloro-6-aryl-picolinoyl acid chlorides as shown in Scheme 2 below. "Ar" represents an aryl group.

Scheme 2

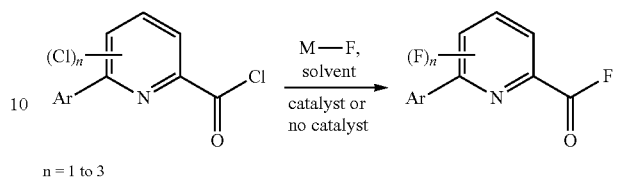

n = 1 to 3

In Scheme 2, "M-F" represents a metal fluoride salt, including but not limited to, sodium fluoride, potassium fluoride or cesium fluoride. In certain embodiments, the solvent is sulfolane or acetonitrile. "Ar" represents an aryl group.

The fluoropicolinoyl fluorides provided herein may be used as intermediates in the preparation of picolinate acids and esters, which in turn may be used as intermediates in the preparation of 4-amino-5-fluoro-3-halo-6-aryl-picolinates such as 4-amino-3-chloro-5-fluoro-6-(4-chloro-2-fluoro-3-methoxyphenyl)pyridine-2-carboxylic acid.

Schemes 3 and 4 are non-limiting examples of the processes provided herein. Carboxylic acid or ester derivatives of the picolinoyl fluorides provided herein may be prepared according to Schemes 3 and 4 as desired products, or to further characterize the picolinoyl fluorides, as in some instances, the picolinoyl fluorides are not stable to certain conventional purification methods. In most cases, the picolinoyl fluorides were characterized by GC/MS and $^{19}$F NMR analysis without purification. 4,5,6-trifluoropicolinoyl fluoride was isolated by distillation and characterized by GC/MS and NMR techniques. The esters and carboxylic acids provided below were purified and characterized by GC/MS and NMR techniques.

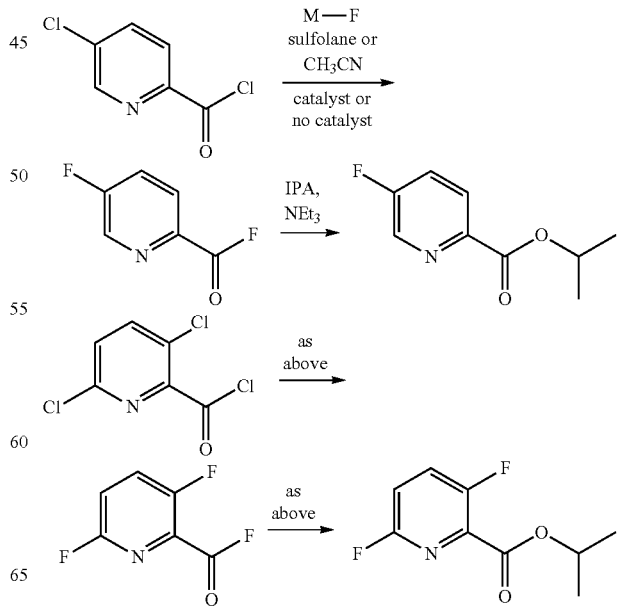

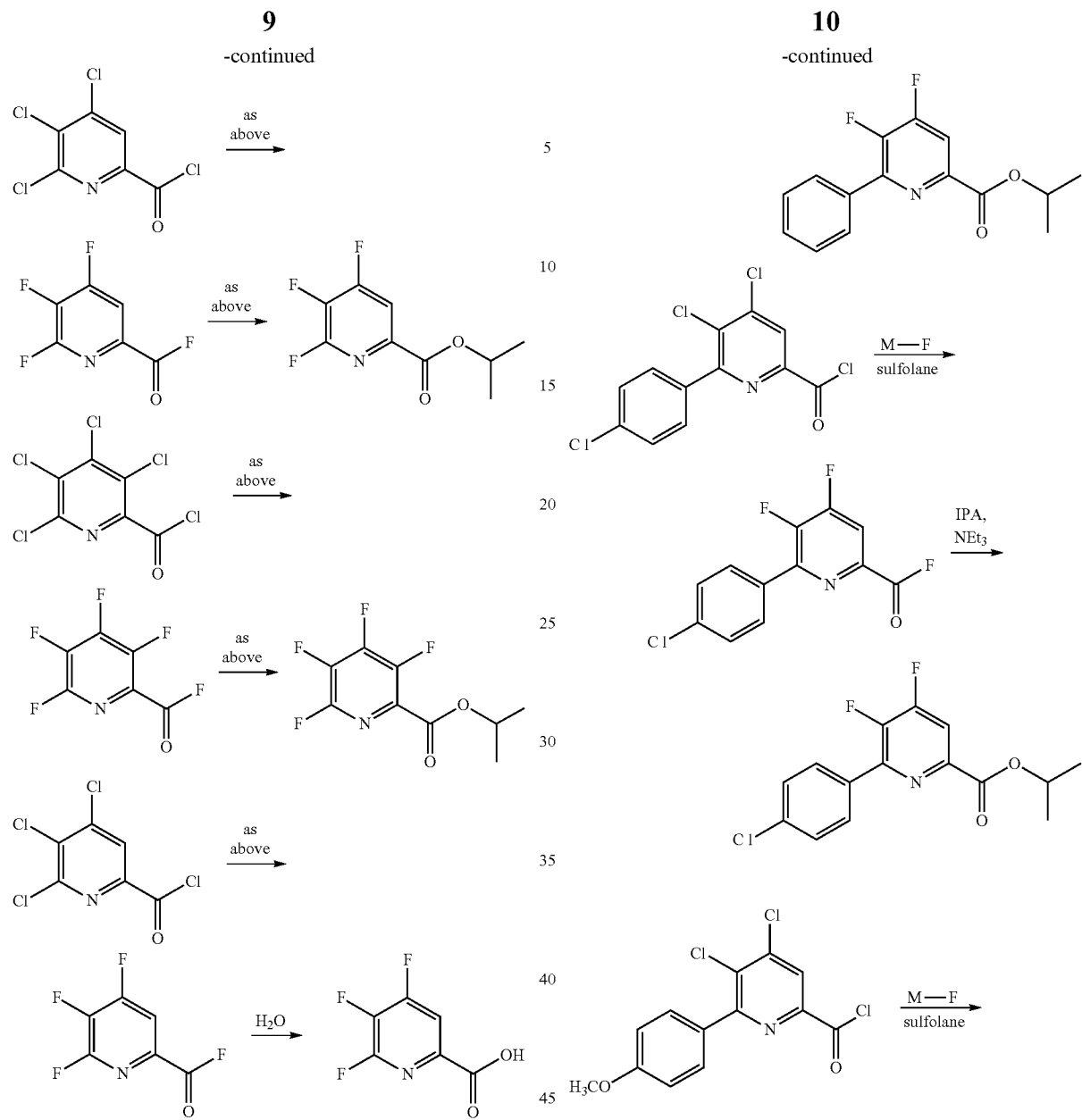
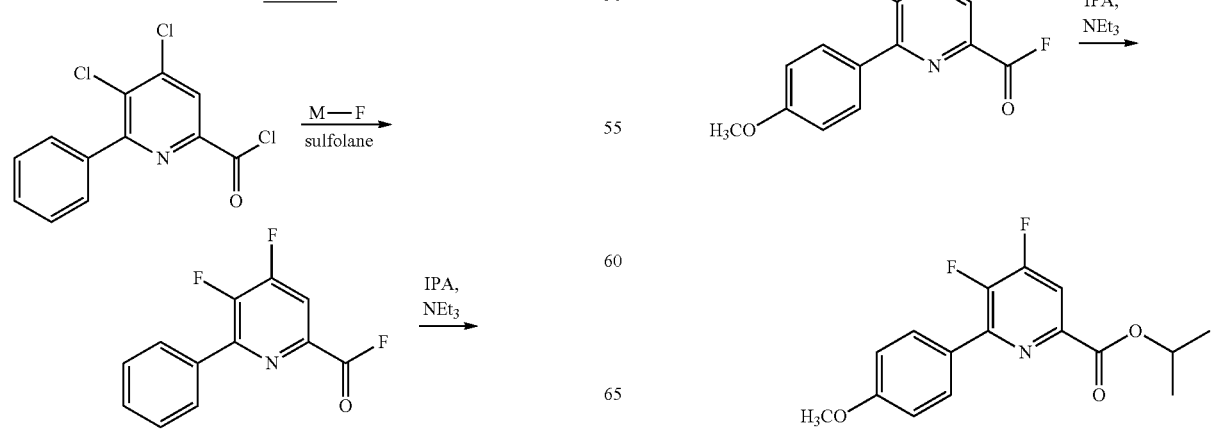

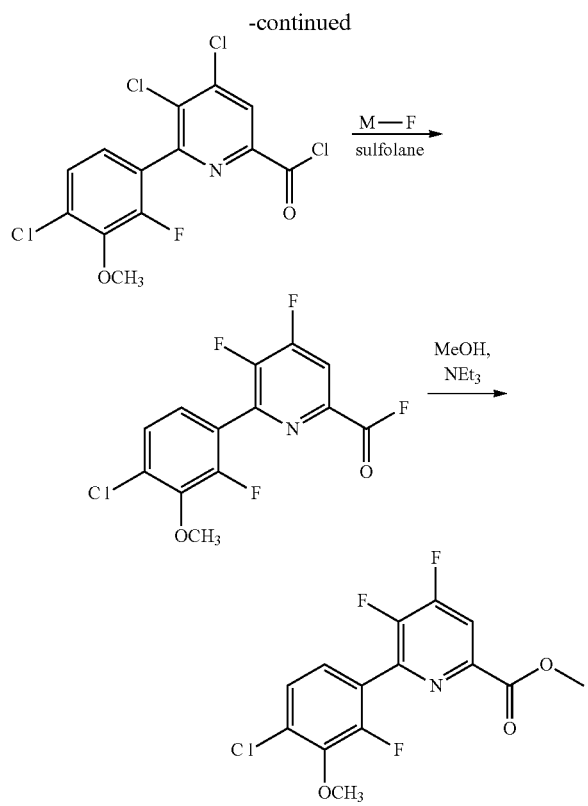

Schemes 3 and 4 provide direct access to di-, tri- and tetra-fluoropicolinoyl fluorides in good yields. Previous methods, as illustrated in Scheme 5, resulted in complex mixtures of undesired products. Thus, the processes provided herein represent and improved process for access to di-, tri- and tetra-fluoropicolinates.

esters, can be prepared by direct esterification or transesterification reactions using techniques which are well known in the art. An exemplary scheme for the preparation of a 6-aryl-picolinoyl chloride is shown below:

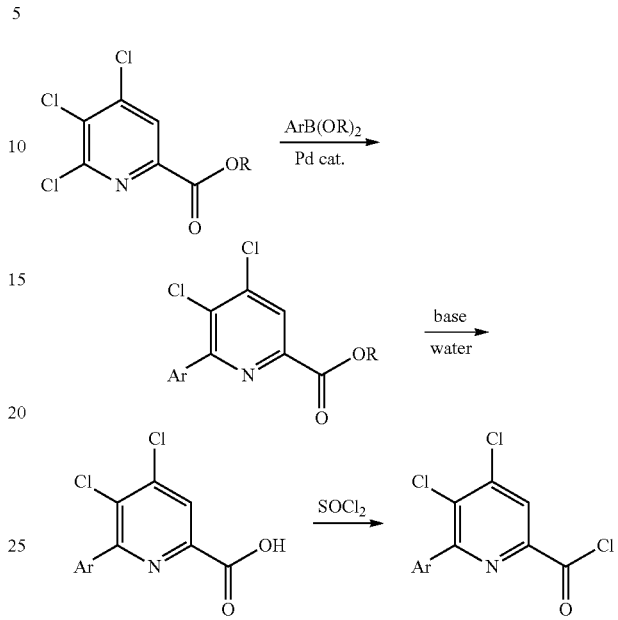

Fluoride ion sources which may be used in processes provided herein include alkali metal fluorides ("M-F"), which include sodium fluoride (NaF), potassium fluoride (KF) and cesium fluoride (CsF). Fluoride salts such as tetrabutylammonium fluoride (n-Bu$_4$NF) may also be used.

In some embodiments, the reactions are carried out in a solvent or reaction medium such as, acetonitrile, sulfolane, alkyl nitriles, polyethers, or alkyl sulfones, including mixtures thereof. In certain embodiments, the solvent used is an

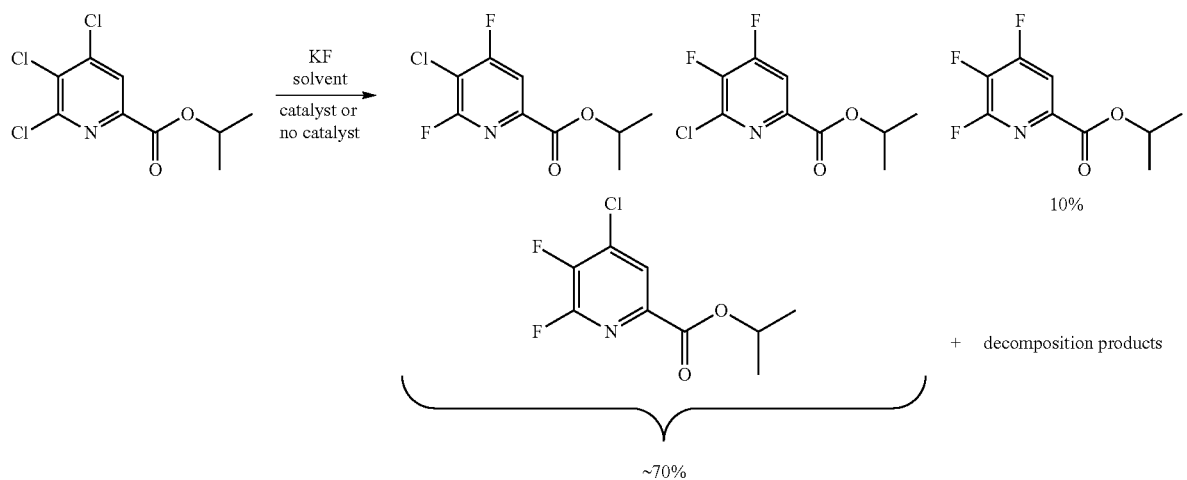

The mono-, di-, tri, and tetra-chloropicolinoyl chloride and/or 6-aryl-picolinoyl chloride starting materials provided herein are known compounds, and/or may be prepared from known chloropicolinates using routine techniques known in the art. See, e.g., U.S. Pat. No. 6,784,137 B2. Higher esters, including unsubstituted or substituted $C_7$-$C_{11}$ arylalkyl alkyl nitrile or an alkyl sulfone. In certain embodiments, the solvent used is acetonitrile or sulfolane.

Catalysts such as crown ethers or phase transfer agents which are known to increase the rate of fluoride exchange may also be used. In some embodiments, the catalyst is a crown ether, a phosphonium halide, a polyether, a phosphazenium salt, or a tetra-substituted ammonium halide. In certain embodiments, the catalyst is a crown ether, e.g., 18-crown-6.

The temperature at which the reaction is conducted is not critical. In certain embodiments, the temperature is from about 50° C. to about 200° C., and in some embodiments, from about 80° C. to about 140° C. Depending upon which solvent is employed in a particular reaction, the optimum temperature will vary. Generally speaking the lower the temperature the slower the reaction will proceed. Exemplary reactions are conducted in the presence of vigorous agitation sufficient to maintain an essentially uniformly dispersed mixture of the reactants.

In conducting the reaction, neither the rate, nor the order, of addition of the reactants is critical. In some embodiments, the solvent and alkali metal fluoride, and optionally, the catalyst, are mixed before the picolinoyl chloride is added to the reaction mixture. In certain embodiments, the reaction requires from about 2 to about 100 hours and is conducted at ambient atmospheric pressure. In some embodiments, the reaction is conducted at a pressure up to and including 500 psi.

While the exact amount of reactants is not critical, in some embodiments an amount of alkali metal fluoride is provided which will supply at least about an equimolar amount of fluorine atoms based on the number of chlorine atoms to be exchanged in the starting material, i.e., at least an equimolar amount of alkali metal fluoride.

The products obtained by any of the processes provided herein may be recovered by conventional means, such as evaporation or extraction, and may be purified by standard procedures, such as distillation, recrystallization or chromatography.

Definitions

The terms "alkyl," "alkenyl" and "alkynyl," as well as derivative terms such as "alkoxy," "acyl," "alkylthio" and "alkylsulfonyl" as used herein, include within their scope straight chain, branched chain and cyclic moieties, and include moieties having one to twelve carbon atoms. In certain embodiments, "alkyl," "alkoxy," "acyl," "alkylthio" and "alkylsulfonyl" each contain one to six carbon atoms or alternatively, one to four carbon atoms. In certain embodiments, "alkenyl" and "alkynyl" each contain two to six carbon atoms or alternatively, two to four carbon atoms.

Unless specifically stated otherwise, each of alkyl, "alkenyl" and "alkynyl," as well as derivative terms such as "alkoxy," "acyl," "alkylthio" and "alkylsulfonyl" may be unsubstituted or substituted with one or more substituents selected from but not limited to halogen, hydroxy, $C_1$-$C_6$ alkoxy, $C_1$-$C_6$ alkylthio, $C_1$-$C_6$ acyl, formyl, cyano, aryloxy or aryl, provided that the substituents are sterically compatible and the rules of chemical bonding and strain energy are satisfied. The terms "alkenyl" and "alkynyl" are intended to include one or more unsaturated bonds.

The term "aryl," as used herein, refers to a 6-14 membered aromatic carbocyclic group, e.g., phenyl or naphthyl. The aryl group may be unsubstituted or substituted with one or more substituents independently selected from halogen, nitro, cyano, $C_1$-$C_6$ alkyl, $C_1$-$C_6$ alkoxy, halogenated $C_1$-$C_6$ alkyl, halogenated $C_1$-$C_6$ alkoxy, $C_1$-$C_6$ alkylthio, $C(O)OC_1$-$C_6$ alkyl, or where two adjacent substituents are taken together as —O(CH$_2$)$_n$O— wherein n=1 or 2.

The term "arylalkyl," as used herein, refers to a phenyl substituted alkyl group having a total of 7 to 11 carbon atoms, such as benzyl (—CH$_2$C$_6$H$_5$), 2-methylnaphthyl (—CH$_2$C$_{10}$H$_7$) and 1- or 2-phenethyl (—CH$_2$CH$_2$C$_6$H$_5$ or —CH(CH$_3$)C$_6$H$_5$). The phenyl group may itself be unsubstituted or substituted with one or more substituents independently selected from halogen, nitro, cyano, $C_1$-$C_6$ alkyl, $C_1$-$C_6$ alkoxy, halogenated $C_1$-$C_6$ alkyl, halogenated $C_1$-$C_6$ alkoxy, $C_1$-$C_6$ alkylthio, $C(O)OC_1$-$C_6$alkyl, or where two adjacent substituents are taken together as —O(CH$_2$)$_n$O— wherein n=1 or 2, provided that the substituents are sterically compatible and the rules of chemical bonding and strain energy are satisfied.

6-Aryl groups provided herein may be substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy. In certain embodiments, the substitution pattern is selected from 4-substituted phenyl, 2,4-disubstituted phenyl, 2,3,4-trisubstituted phenyl, 2,4,5-trisubstituted phenyl, and 2,3,4,6-tetrasubstituted phenyl.

Unless specified otherwise, the term "halogen," as well as derivative terms such as "halo," refers to fluorine, chlorine, bromine and iodine.

6. EXAMPLES

Example 1

4,5,6-trifluoropicolinoyl fluoride

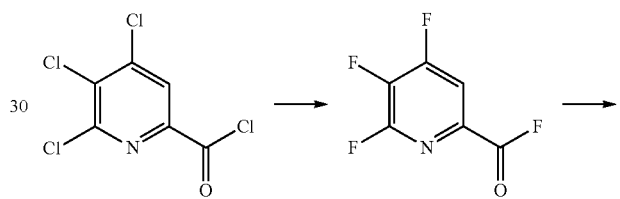

A 1-liter three neck round bottom flask was purged with N$_2$ and fitted with a condenser/N$_2$ bubbler, mechanical stirrer and a stopper. To the reactor was add anhydrous CsF (172 g, 1.13 mol), dry acetonitrile (400 mL), 18-crown-6 (6.0 g, 0.023 mol) and the 4,5,6-trichloropicolinoyl chloride (55 g, 0.23 mol). The mixture was heated to reflux and held there for 20 h. The slurry was cooled to room temperature and the salts filtered under N$_2$ pressure. The salt cake was rinsed with dry acetonitrile (100 mL) to give an amber liquid (372 g). A three neck N$_2$ purged 250 mL round bottom flask with thermowell was fitted with two stoppers, a magnetic stir bar and a vacuum jacketed Vigruex distillation column (15 cm×1 cm) with fraction collector connected to a N$_2$ bubbler. To the vessel was added 140 g of the acetonitrile solution from above. The distillation vessel was heated to 82-85° C. while a clear colorless distillate (acetonitrile) was collected overhead at 80-83° C. When the distillation pot temperature began to rise and the head temperature began to fall the distillation was terminated and allowed to cool to room temperature under N$_2$. The distillation pot residue was quickly transferred to a N$_2$ purged two neck 25 mL round bottom flask. The flask was fitted with a thermometer, magnetic stir bar and the same distillation set up described above. This distillation system could vent to vacuum or N$_2$. Vacuum (ca. 70 mmHg) was established and then heating of the distillation vessel commenced. The product was collected as a clear colorless liquid (6.7 g, bp 55-60° C. @ 55-60 mmHg). GC area percent analysis showed the material to be 99.1% pure: $^1$H NMR (CDCl$_3$, 400 MHz, ppm) δ 8.08 (ddd, J=8.4, 4.4, 0.4 Hz); $^{13}$C NMR (101 MHz, CDCl$_3$, ppm) δ 157.71 (dt, J=269.0, 6.5 Hz), 152.96 (dd, J=246.1, 13.4 Hz), 152.49 (d, J=348.6 Hz), 138.69 (ddd, J=275.3, 30.2, 12.9 Hz), 135.44 (dddd, J=74.6, 15.1, 7.8 Hz), 117.00 (dt, J=18.2, 4.2 Hz); MS (GC, 70 eV electron impact) 179 (M+, 100%), 160 (8%), 151 (100%), 132 (80%), 82 (63%).

In another experiment as described above, after the filtration and salt cake wash, 366 g of amber solution was obtained. Area percent GC analysis indicated the mixture was 86.4% 4,5,6-trifluoropicolinoyl fluoride and 13.6% 18-crown-6. An internal standard GC analysis method was developed using dimethyl phthalate as the internal standard and the material prepared above as the pure component. GC assay of the amber solution indicated it was 9.8 wt. % product which correlated to a yield of 89%.

Example 2

4,5,6-trifluoropicolinic acid

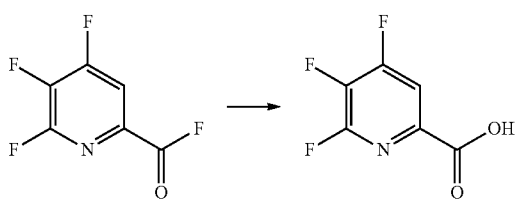 [SMILES: O=C(F)c1cc(F)c(F)c(F)n1 ; O=C(O)c1cc(F)c(F)c(F)n1]

4,5,6-Trifluoropicolinoyl fluoride (300 mg) was allowed to stand in air for six days providing the carboxylic acid (250 mg) as a white solid: mp 81-82° C.; $^1$H NMR (400 MHz, acetone-$d_6$) δ 8.07 (dd, J=9.2, 4.8 Hz); $^{13}$C NMR (101 MHz, acetone-$d_6$) δ 163.4 (d, J=3.2 Hz), 158.6 (ddd, J=263.8, 9.0, 5.8 Hz), 152.9 (ddd, J=237.2, 12.1, 4.7 Hz), 142.2 (m), 138.2 (ddd, J=267.2, 31.4, 13.5 Hz), 115.2 (dd, J=17.6, 5.2 Hz); MS (GC, 70 eV EI) 177 (M+, 1%), 160 (5%), 133 (100%), 132 (40%), 106 (40%), 82 (30%).

Example 3

Isopropyl 3,4,5,6-tetrafluoropicolinate

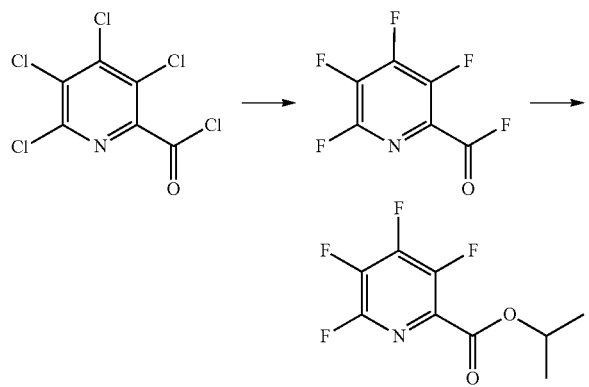

The reaction was carried out in a nitrogen atmosphere glove box. To a glass jar equipped with a stir bar was added 3,4,5,6-tetrachloropicolinoyl chloride (1.117 g, 4 mmol), 18-crown-6 (0.106 g, 0.4 mmol), KF (1.859 g, 32 mmol) and sulfolane (pre-dried, 15 g). The mixture was heated to 130° C. on a heating block for 21 hours. A sample was taken and analyzed by GC, GC/MS and $^{19}$F NMR. GC showed this reaction was complete. GC/MS results were consistent with the chemical formula of 3,4,5,6-tetrafluoropicolinoyl fluoride: 70 eV EIMS (GC) m/z=197 (M+, 91%), 169 (100%), 150 (51%), 100 (100%). $^{19}$F NMR (376 MHz, CD$_3$CN) δ 26.57 (d, J=38.1 Hz), −81.71 (dd, J=44.1, 24.4 Hz), −133.00 to −134.26 (m), −136.54 to −136.69 (m), −145.62 to −145.77 (m).

Anhydrous 2-propanol (0.361 g, 6 mmol) and anhydrous tri-ethylamine (0.405 g, 4 mmol) were added drop-wise at room temperature to the 3,4,5,6-tetrafluoropicolinoyl fluoride provided above. The mixture was stirred at room temperature overnight, poured into a separatory funnel with water and extracted with ethyl ether. The organic phase was then washed with water and dried over MgSO$_4$. The solvent was removed with a rotary evaporator. The concentrated crude product was purified using column chromatography (silica gel) with ethyl acetate/hexanes mixture (1/10) as eluent to give 0.454 g (48% yield, 96% GC purity, 93% LC purity) of desired product as a pale yellow liquid. GC/MS results were consistent with the chemical formula of isopropyl 3,4,5,6-tetrafluoropicolinate: 70 eV EIMS (GC) m/z=196 (31%), 178 (100%), 150 (45%), 100 (26%), 43 (34%). $^1$H NMR (400 MHz, CDCl$_3$) δ 5.32 (hept, J=6.3 Hz, 1H), 1.42 (d, J=6.3 Hz, 6H). $^{13}$C NMR (101 MHz, CDCl$_3$) δ 159.81 to 159.74 (m), 149.22 to 148.78 (m), 148.04 to 147.86 (m), 146.49 to 146.10 (m), 145.65 to 145.47 (m), 138.53 (dd, J=34.3, 11.2 Hz), 135.79 (dd, J=34.4, 11.2 Hz), 129.02 to 128.74 (m), 70.97 (s), 21.60 (s). $^{19}$F NMR (376 MHz, CDCl$_3$) δ −80.31 to −80.49 (m), −136.04 to −136.18 (m), −137.10 to −137.25 (m), −149.81 to −149.95 (m).

Alternatively, the above reaction was performed in acetonitrile rather than sulfolane. A 100 mL Parr reactor (Hastelloy C construction) was cleaned, dried and leak tested under nitrogen. To the vessel was added 3,4,5,6-tetrachloropicolinoyl chloride (5.587 g, 20 mmol), 18-crown-6 (0.529 g, 2 mmol), KF (10.458 g, 180 mmol) and anhydrous acetonitrile (45 g). The entire system was purged with nitrogen. The reaction mixture was stirred at 135° C. for 20 hours, and then was allowed to cool to below 45° C. The system was slowly vented. A sample was taken and analyzed by GC, GC/MS and $^{19}$F NMR. GC showed this reaction was complete. GC/MS results were consistent with the chemical formula of 3,4,5,6-tetrafluoropicolinoyl fluoride: 70 eV EIMS (GC) m/z=197 (M+, 86%), 169 (98%), 150 (51%), 100 (100%). $^{19}$F NMR (376 MHz, CD3CN) δ 26.34 (d, J=38.3 Hz), −81.98 (dd, J=44.2, 23.6 Hz), −134.35 to −134.57 (m), −136.94 to −137.09 (m), −146.02 to −146.17 (m).

Anhydrous 2-propanol (1.803 g, 30 mmol) and anhydrous tri-ethylamine (2.024 g, 20 mmol) were added drop-wise at 5-10° C. to the solution of 3,4,5,6-tetrafluoropicolinoyl fluoride provided above. The mixture was stirred at room temperature overnight. The mixture was discharged from the vessel and the salts were removed by filtration and washed with a little acetonitrile. The solvent was removed with a rotary evaporator. The crude mixture was re-dissolved in ethyl ether. The organic phase was then washed with water and dried over MgSO$_4$. The solvent was removed with a rotary evaporator. The concentrated crude product was purified using column chromatography (silica gel) with ethyl acetate/hexanes mixture (4/50) as eluent to give 3.77 g (79% yield, 99% GC purity, 97% LC purity) of desired product as a pale yellow liquid. GC/MS results were consistent with the chemical formula of isopropyl 3,4,5,6-tetrafluoropicolinate: 70 eV EIMS (GC) m/z=196 (32%), 178 (100%), 150 (49%), 100 (33%), 43 (75%). $^1$H NMR (400 MHz, CDCl$_3$) δ 5.32 (hept, J=6.3 Hz, 1H), 1.42 (d, J=6.3 Hz, 6H). $^{13}$C NMR (101 MHz, CDCl$_3$) δ 159.82 to 159.74 (m), 149.22 to 148.85 (m), 148.02 to 147.89 (m), 146.47 to 146.17 (m), 145.63 to 145.47 (m), 138.54 (dd, J=34.3, 11.2 Hz), 135.79 (dd, J=34.3, 11.4 Hz), 129.03 to 128.74 (m), 70.98 (s), 21.61 (s). $^{19}$F NMR (376 MHz, CDCl$_3$) δ –80.26 to –80.44 (m), –135.99 to –136.13 (m), –137.07 to –137.22 (m), –149.77 to –149.91 (m).

126.78 (d, J=5.4 Hz), 123.31 (d, J=18.5 Hz), 69.71 (s), 21.81 (s). $^{19}$F NMR (376 MHz, CDCl$_3$) δ –120.51.

Example 4

Isopropyl 5-fluoropicolinate

Example 5

Isopropyl 3,6-difluoropicolinate

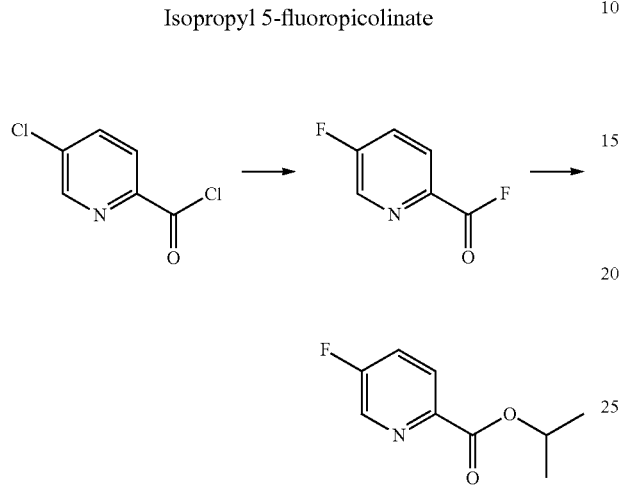

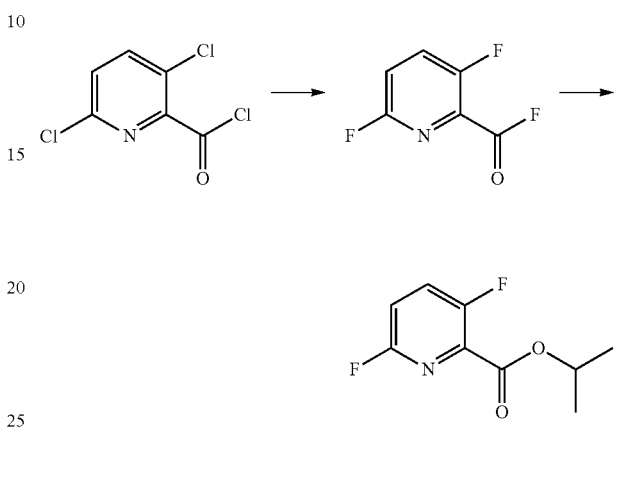

The reaction was carried out in a nitrogen atmosphere glove box. To a glass jar equipped with a stir bar was added 5-chloropicolinoyl chloride (0.704 g, 4 mmol), 18-crown-6 (0.106 g, 0.4 mmol), KF (0.744 g, 12.8 mmol) and sulfolane (pre-dried, 8 g). The mixture was heated to 130° C. on a heating block for 19 hours. A sample was taken and analyzed by GC. The results showed that the reaction was not complete, therefore additional KF (0.232 g, 4 mmol) was added and the mixture was heated to 130° C. for additional 22 hours. A sample was analyzed by GC, GC/MS and $^{19}$F NMR. GC showed this reaction was complete. GC/MS results were consistent with the chemical formula of 5-fluoropicolinoyl fluoride: 70 eV EIMS (GC) m/z=143 (M$^+$, 100%), 115 (55%), 96 (90%), 76 (46%). $^{19}$F NMR (376 MHz, CD$_3$CN) δ 16.01 (s), –117.57 (s).

Anhydrous 2-propanol (0.361 g, 6 mmol) and anhydrous tri-ethylamine (0.405 g, 4 mmol) were added drop-wise at room temperature to the 5-fluoropicolinoyl fluoride provided above. The mixture was stirred at room temperature overnight, poured into a separatory funnel with water and extracted with ethyl ether. The organic phase was then washed with water and dried over MgSO$_4$. The solvent was removed with a rotary evaporator. The concentrated crude product was purified using column chromatography (silica gel) with ethyl acetate/hexanes mixture (1/10) as eluent to give 0.17 g (23% yield, 96% LC purity) of desired product as an off-white solid. GC/MS results were consistent with the chemical formula of isopropyl 5-fluoropicolinate: 70 eV EIMS (GC) m/z=142 (43%), 124 (100%), 97 (97%), 96 (93%), 43 (59%). $^1$H NMR (400 MHz, CDCl$_3$) δ 8.60 (d, J=2.8 Hz, 1H), 8.18 (dd, J=8.8, 4.4 Hz, 1H), 7.52 (ddd, J=8.7, 7.9, 2.9 Hz, 1H), 5.34 (hept, J=6.3 Hz, 1H), 1.43 (d, J=6.3 Hz, 6H). $^{13}$C NMR (101 MHz, CDCl$_3$) δ 163.63 (s), 162.32 (s), 159.71 (s), 144.84 (d, J=3.8 Hz), 138.46 (d, J=24.8 Hz), The reaction was carried out in a nitrogen atmosphere glove box. To a glass jar equipped with a stir bar was added 3,6-dichloropicolinoyl chloride (0.842 g, 4 mmol), 18-crown-6 (0.106 g, 0.4 mmol), KF (1.394 g, 24 mmol) and sulfolane (pre-dried, 9 g). The mixture was heated to 130° C. on a heating block for 22 hours. A sample was taken and analyzed by GC. The results showed that the reaction was not complete, therefore additional KF (0.348 g, 6 mmol) was added and mixture was heated to 130° C. for additional 22 hours. A sample was analyzed by GC, GC/MS and $^{19}$F NMR. GC showed this reaction was complete. GC/MS results were consistent with the chemical formula of 3,6-difluoropicolinoyl fluoride: 70 eV EIMS (GC) m/z=161 (M$^+$, 73%), 133 (100%), 114 (44%), 64 (60%). $^{19}$F NMR (376 MHz, CD$_3$CN) δ 26.30 (d, J=36.4 Hz), –70.56 (d, J=25.9 Hz), –119.36 (dd, J=36.4, 26.0 Hz).

Anhydrous 2-propanol (0.361 g, 6 mmol) and anhydrous tri-ethylamine (0.405 g, 4 mmol) were added dropwise at room temperature to the 3,6-difluoropicolinoyl fluoride provided above. The mixture was stirred at room temperature for 6 hours, poured into a separatory funnel with water and extracted with ethyl ether. The organic phase was then washed with water and dried over MgSO$_4$. The solvent was removed with a rotary evaporator. The concentrated crude product was purified using column chromatography (silica gel) with ethyl acetate/hexanes mixture (1/10) as eluent to give 0.39 g (48% yield, 99% GC purity, 98% LC purity) of desired product as a pale yellow liquid. GC/MS results were consistent with the chemical formula of isopropyl 3,6-difluoropicolinate: 70 eV EIMS (GC) m/z=160 (41%), 142 (100%), 115 (43%), 114 (66%), 64 (31%), 43 (51%). $^1$H NMR (400 MHz, CDCl$_3$) δ 7.69 to 7.63 (m, 1H), 7.16 to 7.12 (m), 5.33 (hept, J=6.3 Hz, 1H), 1.41 (d, J=6.3 Hz, 6H). $^{13}$C NMR (101 MHz, CDCl$_3$) δ 161.41 (d, J=6.3 Hz), 158.80 (d, J=1.2 Hz), 158.26 (d, J=4.3 Hz), 156.41 (d, J=1.2 Hz), 155.62 (d, J=4.4 Hz), 134.05 (t, J=13.5 Hz), 131.06 (dd, J=23.9, 8.3 Hz), 114.86 (dd, J=41.7, 5.9 Hz), 70.34 (s), 21.71 (s). $^{19}$F NMR (376 MHz, CDCl$_3$) δ−69.40 (d, J=26.9 Hz), −122.76 (d, J=27.4 Hz).

Example 6

Isopropyl 4,5-difluoro-6-(4-chlorophenyl)picolinate

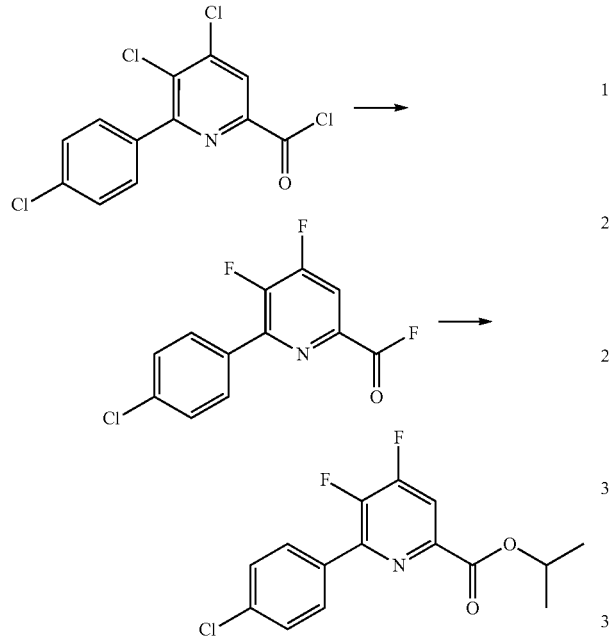

To a solution of 4,5-dichloro-6-(4-chlorophenyl)picolinoyl chloride (2.0 g, 6.23 mmol) in sulfolane (40 mL, dried over 4 Å molecular sieves, 100 ppm H$_2$O) was added potassium fluoride (2.2 g, 37.4 mmol). The reaction mixture was heated at 130° C. for 24 h. Reaction mixture was analyzed by GC-MS and $^{19}$F NMR. (Data for 6-(4-chlorophenyl)-4,5-difluoropicolinoyl fluoride, GC-MS: m/z=271, 223; $^{19}$F NMR (376 MHz, Toluene-d$_8$) δ 17.05 (s), −123.81 (d, J=19.1 Hz), −140.17 (d, J=19.1 Hz). Reaction was allowed to cool to room temperature and triethylamine (1.1 mL, 7.8 mmol) and isopropanol (0.7 mL, 9.4 mmol) were added. After stirring for 1.5 h, the reaction mixture was diluted with water (100 mL) and transferred to a separatory funnel. The reaction mixture was extracted with methyl tert-butyl ether (MTBE, 2×50 mL). The combined organic extracts were washed with water (3×50 mL) and saturated aqueous NaCl solution (50 mL) and concentrated under reduced pressure to provide a brown oil. The crude product oil was purified by silica gel flash chromatography (hexane/ethyl acetate gradient, 100% hexane→20% hexane/ethyl acetate) to provide 0.93 g (48% yield) of isopropyl 6-(4-chlorophenyl)-4,5-difluoropicolinate as a white solid. $^1$H NMR (400 MHz, CDCl$_3$) δ 8.04-7.98 (m, 2H), 7.90 (dd, J=9.4, 5.3 Hz, 1H), 7.51-7.45 (m, 2H), 5.31 (hept, J=6.3 Hz, 1H), 1.43 (d, J=6.3 Hz, 6H). $^{13}$C NMR (101 MHz, CDCl$_3$) δ 162.72 (d, J=3.5 Hz), 158.12 (d, J=12.6 Hz), 155.49 (d, J=12.4 Hz), 149.41 (d, J=11.0 Hz), 147.16 (dd, J=7.9, 1.0 Hz), 146.73 (d, J=10.9 Hz), 136.51 (d, J=0.9 Hz), 130.34 (d, J=6.6 Hz) 128.93 (s), 113.80 (d, J=16.1 Hz), 70.25 (s), 21.85 (s). 19F NMR (376 MHz, CDCl$_3$) δ−124.73 (dd, J=17.7, 9.5 Hz), −144.38 (dd, J=17.7, 5.4 Hz). LRMS. Calcd. C$_{16}$H$_{15}$F$_2$NO$_3$: 307.10. Found: m/z=307 (M$^+$), 221, 206. MP. 73-74° C.

Example 7

Isopropyl 4,5-difluoro-6-phenylpicolinate

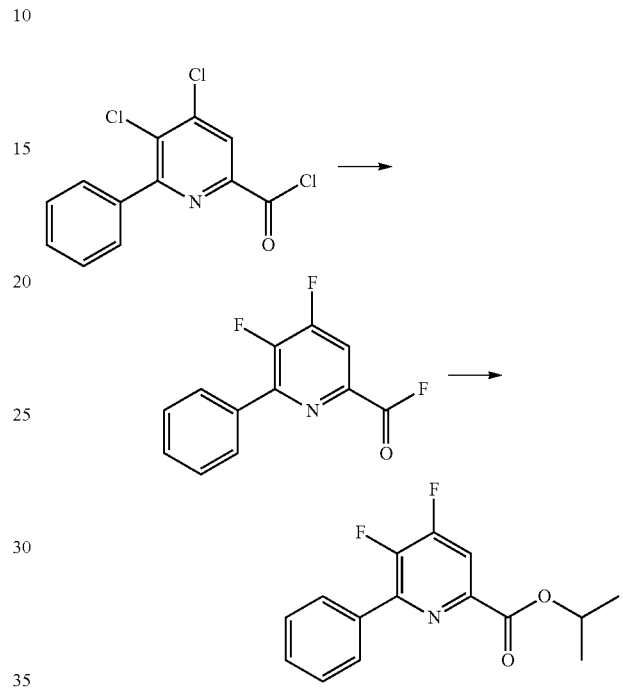

To a solution of 4,5-dichloro-6-phenylpicolinoyl chloride (1.76 g, 6.14 mmol) in sulfolane (40 mL, dried over 4 Å molecular sieves, ~100 ppm H$_2$O) was added potassium fluoride (2.14 g, 36.9 mmol). The reaction mixture was heated at 130° C. for 24 h. Reaction mixture was analyzed by GC-MS and $^{19}$F NMR. (Data for 4,5-difluoro-6-phenylpicolinoyl fluoride, GC-MS: m/z=237, 189; $^{19}$F NMR (376 MHz, Toluene-d8) δ 17.03 (s), −124.14 (d, J=19.1 Hz), −140.76 (d, J=19.1 Hz). Reaction was allowed to cool to room temperature and triethylamine (1.1 mL, 7.7 mmol) and isopropanol (0.7 mL, 9.2 mmol) were added. After stirring for 1.5 h, the reaction mixture was diluted with water (100 mL) and transferred to a separatory funnel. The reaction mixture was extracted with methyl tert-butyl ether (MTBE, 2×50 mL). The combined organic extracts were washed with water (3×50 mL) and saturated NaCl (50 mL) and concentrated under reduced pressure to provide a brown oil. The crude product oil was purified by silica gel flash chromatography (hexane/ethyl acetate gradient, 100% hexane→20% hexane/ethyl acetate) to provide 1.2 g (70% yield) of isopropyl 4,5-difluoro-6-phenyl-picolinate as a yellow oil. $^1$H NMR (400 MHz, CDCl$_3$) δ 8.07-7.99 (m, 2H), 7.89 (dd, J=9.4, 5.3 Hz, 1H), 7.56-7.42 (m, 3H), 5.31 (hept, J=6.3 Hz, 1H), 1.43 (d, J=6.3 Hz, 6H). $^{13}$C NMR (101 MHz, CDCl$_3$) δ 162.89 (d, J=3.4 Hz), 156.74 (dd, J=264.2, 12.5 Hz), 148.07 (dd, J=268.9, 10.8 Hz), 146.99 (dd, J=309.2, 10.8 Hz), 145.45 (s), 134.12-133.60 (m), 130.20 (s), 129.05 (d, J=5.9 Hz), 128.64 (s), 113.56 (d, J=16.0 Hz), 70.14 (s), 21.86 (s). $^{19}$F NMR (376 MHz, CDCl$_3$) δ−125.22 (dd, J=17.7, 9.5 Hz), −144.74 (dd, J=17.7, 5.4 Hz). LRMS. Calcd. $C_{15}H_{13}F_2$—$NO_2$: 277.09. Found: m/z=277 (M+), 218, 191.

Example 8

Isopropyl 4,5-difluoro-6-(4-methoxyphenyl)picolinate

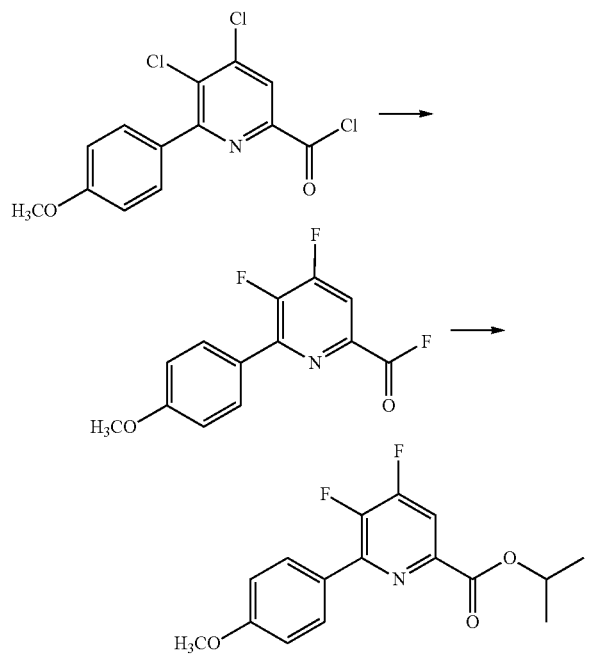

To a solution of 4,5-dichloro-6-(4-methoxyphenyl)-picolinoyl chloride (2.5 g, 7.9 mmol) in sulfolane (40 mL, dried over 4 Å molecular sieves, 100 ppm of water) was added potassium fluoride (2.75 g, 47.4 mmol). The reaction mixture was heated at 150° C. for 24 h. Additional potassium fluoride (1.4 g, 24 mmol) was added and reaction mixture was heated at 150° C. for an additional 24 h. Reaction mixture was analyzed by GC-MS and $^{19}$F NMR. (Data for 4,5-difluoro-6-(4-methoxyphenyl)-picolinoyl fluoride, GC-MS: m/z=267, 224, 176; $^{19}$F NMR (376 MHz, toluene) δ 16.94 (s), −124.65 (d, J=19.1 Hz), −141.23 (d, J=19.1 Hz). Reaction was allowed to cool to room temperature and triethylamine (1.4 mL, 9.9 mmol) and isopropanol (0.9 mL, 11.9 mmol) were added. After stirring for 1.5 h, the reaction mixture was diluted with water (125 mL) and transferred to a separatory funnel. The reaction mixture was extracted with methyl tert-butyl ether (MTBE, 2×75 mL). The combined organic extracts were washed with water (3×75 mL) and saturated NaCl (75 mL) and concentrated under reduced pressure to provide a brown oil. The crude product oil was purified by silica gel flash chromatography (hexane/ethyl acetate gradient, 100% hexane→20% hexane/ethyl acetate) to provide 0.60 g (25% yield) of isopropyl 4,5-difluoro-6-(4-methoxyphenyl)-picolinate as a pale yellow solid. $^1$H NMR (400 MHz, CDCl$_3$) δ 8.08-8.01 (m, 2H), 7.82 (dd, J=9.5, 5.2 Hz, 1H), 7.04-6.97 (m, 2H), 5.30 (hept, J=6.3 Hz, 1H), 3.86 (s, 3H), 1.42 (d, J=6.3 Hz, 6H), $^{13}$C NMR (101 MHz, CDCl$_3$) δ 162.93 (s), 161.22 (s), 156.68 (d, J=263.5, 12.7 Hz), 147.70 (dd, J=267.9, 10.9 Hz), 146.61 (dd, J=286.4, 10.5 Hz), 145.18 (s), 130.53 (d, J=6.6 Hz), 126.43, 114.02 (s), 112.77 (d, J=16.1 Hz), 69.99 (s), 55.32 (s), 21.82 (s). $^{19}$F NMR (376 MHz, CDCl$_3$) δ−125.81 (d, J=17.7 Hz), −145.30 (d, J=19.1 Hz), LRMS. Calcd. for $C_{16}H_{15}F_2NO_3$: 307.10. Found: m/z=307 (M+), 221, 206.

Example 9

Methyl 6-(4-chloro-2-fluoro-3-methoxyphenyl)-4,5-difluoro-2-pyridinecarboxylate

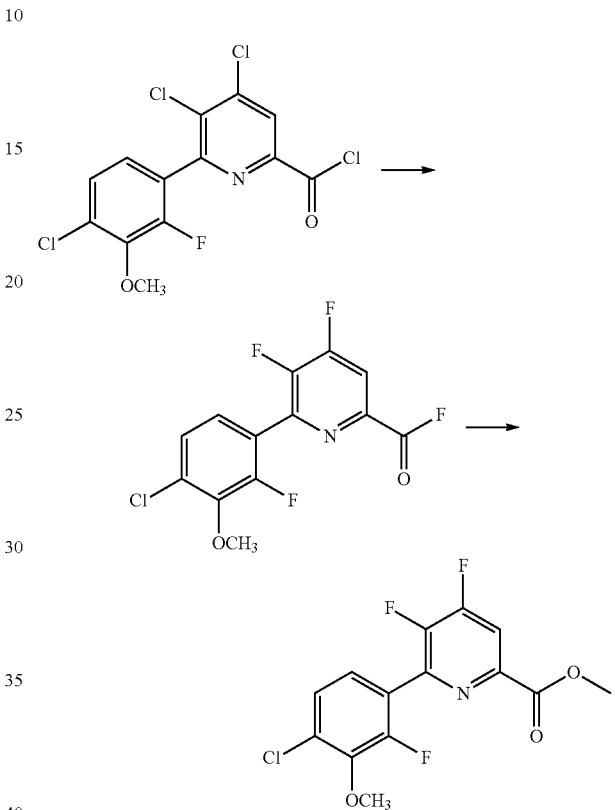

A mixture of 1.74 g (30 mmol, 6 eq) of KF (dried 115° C. with N$_2$ purge overnight), 1.85 g (5 mmol) of 6-(4-chloro-2-fluoro-3-methoxyphenyl)-4,5-dichloro-2-pyridinecarbonyl chloride and 10 mL of sulfolane (dried using 4 Å molecular sieves) was heated at 130° C. for 10 h and then at room temperature overnight. LC area analysis indicated incomplete reaction (63% product, 15% mono-fluoro intermediates). The mixture was heated at 130° C. for another 7 h, when LC area analysis indicated 74% product and 4% mono-fluoro intermediates. After cooling to 50° C., 0.24 mL (6 mmol) of MeOH was added, and the mixture stirred at room temperature overnight. To the amber mixture was added 10 mL of H$_2$O dropwise over 20 min. Initially, gummy solids formed which eventually dissipated to leave a thick, brownish gray mixture. After stirring at room temperature for 15 min, the mud-like mixture was filtered (slow), rinsed with 4 mL of 1:1 sulfolane/H$_2$O and 2× with 4 mL of H$_2$O to give 5.44 g of a brown solid. The solid was dried to give 1.54 g of a tan powder. LC internal standard analysis indicated a purity of 78.4 wt %, for a yield of 73.0%.

Purification of Methyl 6-(4-chloro-2-fluoro-3-methoxyphenyl)-4,5-difluoro-2-pyridinecarboxylate Material from a previous experiment (1.8 g, 67 area % LC) was heated and dissolved in 15 mL of toluene. This solution was flash chromatographed on silica (500 g, 70-230 mesh) eluting with toluene. After 10 L of toluene has passed through the column, product was seen and collected over the next 2 L of eluent. The toluene fractions containing the product were concentrated in vacuo to give 647 mg of a white solid, 94 area % purity by LC analysis. This solid was dissolved in 3 mL of acetonitrile, cooled in a refrigerator, filtered and rinsed with 0.5 mL of cold acetonitrile to give 529 mg of a white solid, mp 134-134° C., 97 area % purity by LC analysis. EIMS m/e (relative intensity) 331 (1Cl, 50), 273 (1Cl, 100), 238 (46), 237 (28), 222 (14), 194 (48); $^1$H NMR (400 MHz, CDCl$_3$) δ 8.05 (dd, J=9, 6 Hz, 1 H), 7.35-7.27 (m, 2 H), 4.01 (s, 3 H), 4.00 (d, J=1 Hz, 3 H); $^{19}$F NMR (376 MHz, $^1$H decoupled, CDCl$_3$) δ −123.64 (d, J=20 Hz), −128.51 (d, J=31 Hz), −139.59 (dd, J=31, 20 Hz); $^{19}$F NMR (376 MHz, CDCl$_3$) δ −123.64 (dd, J=19, 9 Hz), −128.51 (dd, J=31, 6 Hz), −139.59 (ddd, J=31, 19, 6 Hz).

Preparation of Intermediates: 6-aryl-chloropicolinoyl chlorides

Example 10

Isopropyl 4,5-dichloro-6-phenylpicolinate

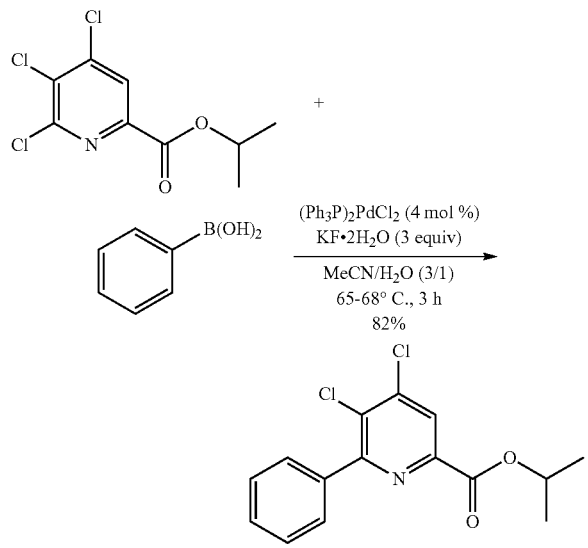

In a 125 mL three-neck round bottom flask was charged potassium fluoride dihydrate (4.52 g, 38.0 mmol), phenylboronic acid (4.88 g, 40 mmol), isopropyl 4,5,6-trichloropicolinate ester (4.28 g, 16.0 mmol), MeCN (60 mL), and H$_2$O (20 mL). The resulting suspension was sparged with N$_2$ for 15 min then bis-triphenylphosphinepalladium (II) chloride (0.45 g, 0.64 mmol) added. The resulting yellow suspension was then sparged for 15 min then heated to 65-68° C. After 1 h of stirring an aliquot (1-2 μL) was taken and diluted with MeCN (2 mL). The aliquot was analyzed by HPLC by monitoring the consumption of starting material isopropyl 4,5,6-trichloropicolinate ester. After 3 h the reaction was deemed complete. The heating mantle was removed and the mixture cooled to ambient temperature and diluted with MeCN/EtOAc/H$_2$O (150 mL, 2/2/1). The layers were then separated using a separating funnel and to the organic layer was added silica gel ≈22 g. The solvent was removed in vacuo and the solid purified by CombiFlash using a 220 g column. Concentration of the aliquots gave a white solid weighing 4.07 g (82%). MP=94-96° C.; $^1$H NMR (400 MHz, CDCl$_3$) δ 8.12 (s, 1 H, pyridine H), 7.74-7.71 (m, 2 H), 7.49-7.46 (m, 3 H), 5.31 (h, J=6.4 Hz, 1 H), 1.41 (d, J=6.4 Hz, 6H); $^{13}$C NMR (100.6 MHz, CDCl$_3$) δ163.1, 158.6, 146.5, 144.3, 137.5, 132.1, 129.6, 129.4, 128.0, 125.0, 70.2, 21.8; LRMS Calcd. For C$_{15}$H$_{13}$Cl$_2$N$_2$O$_2$: 309.03. Found: 309 (M$^+$), 223 (M$^+$-CO$_2$$_1$Pr), 188, 152, 125.

Example 11

4,5-Dichloro-6-phenylpicolinic acid

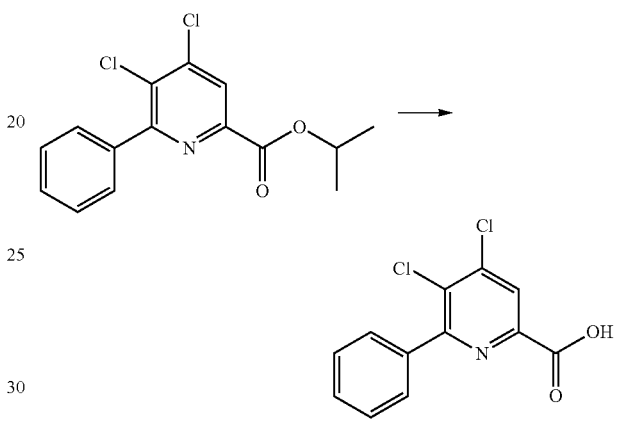

To a 125 mL 3-neck round bottom flask fitted with a condenser, nitrogen inlet, overhead stirring, thermometer and heating mantle was charged isopropyl 4,5-dichloro-6-phenyl picolinate (7.0 g, 22.5 mmol) and isopropyl alcohol (65 mL). Reaction mixture was heated to 40° C. and potassium hydroxide (85%, 5.1 g, 77.4 mmol) and water (5 mL) were added. Solids precipitated from the mixture and it became difficult to stir. The mixture was diluted with water (250 mL) to dissolve most of the solids and allowed to stir at room temperature. Concentrated sulfuric acid (5 mL) was added dropwise to the reaction mixture to achieve a pH of ~2 and solids precipitated from the mixture. The solids were isolated by vacuum filtration and washed with water (2×100 mL), then allowed to dry in a hood. 5.8 g (96% yield) of 4,5-dichloro-6-phenyl picolinic acid was isolated as a white solid. $^1$H NMR (400 MHz, CDCl$_3$) δ 8.28 (s, 1H), 7.74-7.60 (m, 2H), 7.59-7.45 (m, 3H), 5.98 (br s, 1H). $^{13}$C NMR (101 MHz, CDCl$_3$) δ 162.97, 157.76, 146.26, 144.00, 136.51, 133.84, 130.02, 129.26, 128.38, 124.16, MP. 159-160° C.

Example 12

4,5-dichloro-6-phenylpicolinoyl chloride

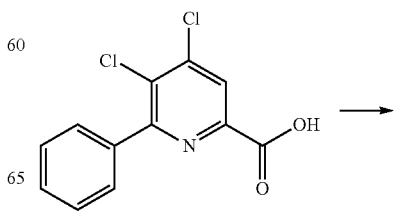

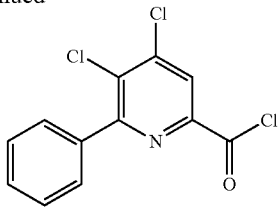

To a mixture of 4,5-dichloro-6-phenylpicolinic acid (3.00 g, 11.2 mmol) in toluene (40 mL) was added thionyl chloride (1.22 mL, 16.8 mmol) and dimethylformamide (0.04 mL, 0.6 mmol). Reaction mixture was heated at 80° C. for 3 h. HPLC analysis of an aliquot treated with methanol and dimethylaminopyridine indicated complete conversion of the starting material. Reaction was allowed to cool to room temperature and then concentrated under reduced pressure to provide a white solid. Toluene (40 mL) was added to dissolve the solid and concentrated under reduced pressure and then this process was performed a second time. 4,5-Dichloro-6-phenylpicolinoyl chloride was isolated as a white solid (2.84 g, 89% yield). $^1$H NMR (400 MHz, CDCl$_3$) δ 8.14 (s, 1H), 7.83-7.75 (m, 2H), 7.55-7.47 (m, 3H). $^{13}$C NMR (101 MHz, CDCl$_3$) δ 168.80, 158.88, 146.42, 145.21, 136.79, 134.40, 129.98, 129.61, 128.31, 124.74, LRMS Calcd. C$_{12}$H$_6$Cl$_3$NO: 284.95. Found: m/z=285 (M$^+$), 250 (M$^+$-Cl), 222, 187, 152, MP. 106-111° C.

Example 13

Isopropyl 4,5-dichloro-6-(4-methoxyphenyl)picolinate

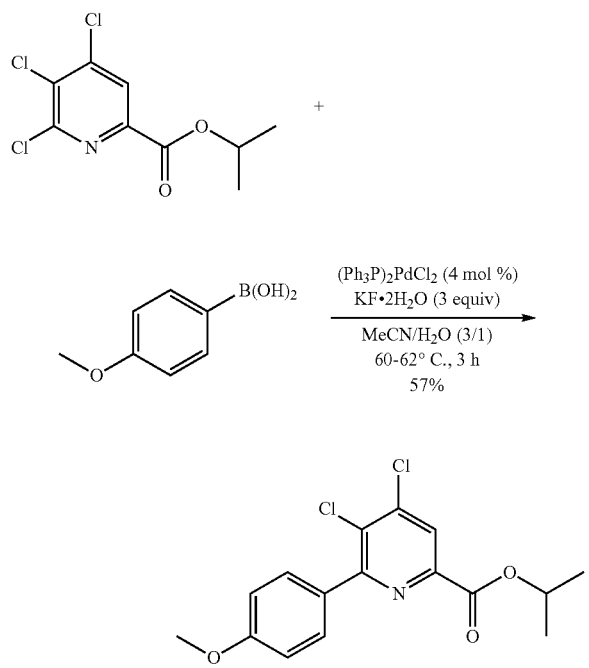

In a 125 mL three-neck round bottom flask was charged potassium fluoride dihydrate (5.65 g, 60.0 mmol), 4-methoxyphenylboronic acid (3.42 g, 22.5 mmol), isopropyl 4,5,6-trichloropicolinate ester (4.00 g, 15.0 mmol), MeCN (72 mL), and H$_2$O (24 mL). The resulting suspension was sparged with N$_2$ for 15 min then bis-triphenylphosphinepalladium (II) chloride (0.42 g, 0.60 mmol) was added. The resulting yellow suspension was then sparged for 15 min then heated to 60-62° C. After 1 h of stirring an aliquot (1-2 µL) was taken and diluted with MeCN (2 mL). The aliquot was analyzed by HPLC by monitoring the consumption of starting isopropyl 4,5,6-trichloropicolinate ester. After 3 h the reaction was deemed complete. The heating mantle was removed and the mixture cooled to ambient temperature and diluted with MeCN/PhMe/H$_2$O (100 mL, 4/3/3). The layers were then separated and to the organic layer was added silica gel≈22 g. The solvent was removed in vacuo and the solid was purified by CombiFlash to give a white solid weighing 2.90 g (57%). MP=113-116° C.; $^1$H NMR (400 MHz, CDCl$_3$) δ 8.07 (s, 1 H, pyridine H), 7.74 (dt, J=9.2, 2.8 Hz, 2 H), 6.99 (dt, J=8.8, 2.8 Hz, 2 H), 5.30 (h, J=6.0 Hz, 1 H), 1.41 (d, J=6.0 Hz, 6 H); $^{13}$C NMR (100.6 MHz, CDCl$_3$) δ 163.2, 160.6, 158.1, 146.4, 144.2, 131.7, 131.2, 129.9, 124.4, 113.4, 70.1, 55.3, 21.8; LRMS Calcd. For C$_{16}$H$_{15}$Cl$_2$NO$_3$: 339.04. Found: 339 (M$^+$), 253 (M$^+$-O$^i$Pr), 218, 203, 182.

Example 14

4,5-Dichloro-6-(4-methoxyphenyl)picolinic acid

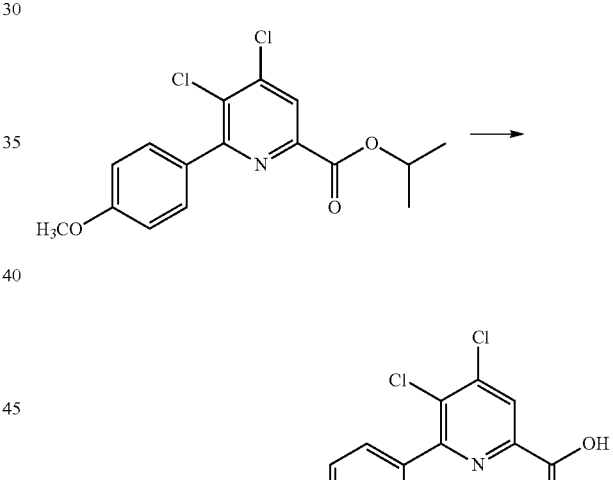

To a mixture of isopropyl 4,5-dichloro-6-(4-methoxyphenyl)picolinate (5.25 g, 15.4 mmol) in tetrahydrofuran (40 mL) and water (10 mL) was added potassium hydroxide (1.26 g, 22.4 mmol). The reaction was allowed to stir at room temperature for 12 h. After 1 hour of stirring, solids precipitated from the mixture. HCl (aq) (2N, 25 mL) was added to the reaction mixture to form a clear biphasic mixture. The mixture was added to water (75 mL) in a separatory funnel and extracted with EtOAc (2×75 mL). The combined organic layers were washed with water (25 mL) and saturated NaCl (50 mL) and then concentrated under reduced pressure to provide 4.57 g (99% yield) of 4,5-dichloro-6-(4-methoxyphenyl)picolinic acid as a white solid. $^1$H NMR (400 MHz, CDCl$_3$) δ 8.23 (s, 1H), 7.72-7.64 (m, 2H), 7.07-6.99 (m, 2H), 3.89 (s, 3H). $^{13}$C NMR (101 MHz, CDCl$_3$) δ 162.78, 161.05, 157.26, 146.30, 143.76, 133.54, 130.98, 128.72, 123.45, 113.77, 55.48; mp=164-181° C.

Example 15

4,5-Dichloro-6-(4-methoxyphenyl)picolinoyl chloride

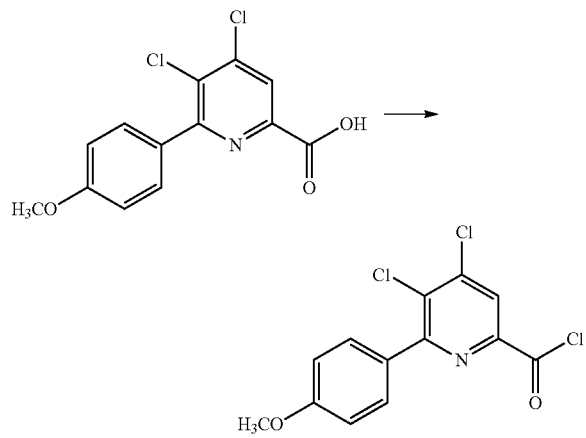

To a mixture of 4,5-dichloro-6-(4-methoxyphenyl)-picolinic acid (4.50 g, 15.1 mmol) in toluene (40 mL) was added thionyl chloride (1.65 mL, 22.6 mmol) and dimethylformamide (0.06 mL, 0.8 mmol). Reaction mixture was heated at 80° C. for 12 h. HPLC analysis of an aliquot treated with methanol and dimethylaminopyridine indicated complete conversion of the starting material. Reaction mixture was allowed to cool to room temperature and concentrated under reduced pressure to provide a yellow solid. Toluene (40 mL) was added to dissolve the solid and concentrated under reduced pressure and then this process was performed a second time. 4,5-Dichloro-6-(4-methoxyphenyl)-picolinoyl chloride was isolated as a yellow solid (4.64 g, 97% yield). $^1$H NMR (400 MHz, CDCl$_3$) δ 8.09 (s, 1H), 7.85-7.77 (m, 2H), 7.06-6.98 (m, 2H). $^{13}$C NMR (101 MHz, CDCl$_3$) δ 168.91, 161.06, 158.35, 146.26, 145.13, 133.92, 131.35, 129.16, 124.13, 113.70, LRMS. Calcd. for $C_{13}H_8Cl_3NO_2$: 314.96. Found: m/z=253 (M$^+$-COCl), 218.

Example 16

Isopropyl 4,5-dichloro-6-(4-chlorophenyl)picolinate

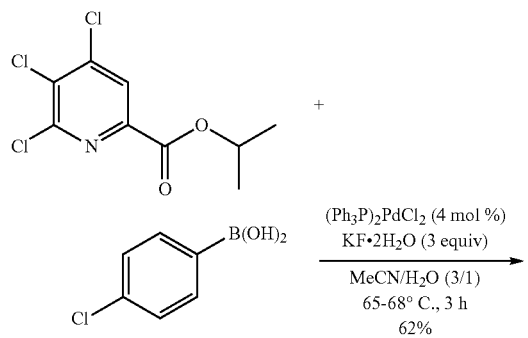

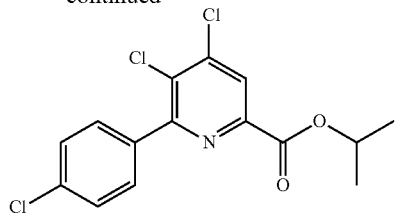

In a 125 mL three-neck round bottom flask was charged potassium fluoride dihydrate (4.52 g, 38.0 mmol), 4-chlorophenylboronic acid (5.00 g, 32.0 mmol), isopropyl 4,5,6-trichloropicolinate ester (4.28 g, 16.0 mmol), MeCN (70 mL), and H$_2$O (23 mL). The resulting suspension was sparged with N$_2$ for 15 min then bis-triphenylphosphinepalladium (II) chloride (0.45 g, 0.64 mmol) added. The resulting yellow suspension was then sparged for 15 min then heated to 65-68° C. After 1 h of stirring an aliquot (1-2 µL) was taken and diluted with MeCN (2 mL). The aliquot was analyzed by HPLC by monitoring the consumption of starting isopropyl 4,5,6-trichloropicolinate ester. After 3 h the reaction was deemed complete. The heating mantle was removed and the mixture cooled to ambient temperature and diluted with MeCN/PhMe/H$_2$O (80 mL, 2/3/2). The layers were then separated and to the organic layer was added silica gel ≈ 22.5 g. The solvent was removed in vacuo and solid purified by CombiFlash to afford after solvent concentration white solid weighing 3.44 g (62%). mp=133-135° C.; $^1$H NMR (400 MHz, CDCl$_3$) δ 8.13 (s, 1 H, pyridine H), 7.69 (dt, J=8.8, 2.0 Hz, 2H), 7.29 (dd, J=8.4, 2.0 Hz, 2 H), 5.31 (h, J=6.0 Hz, 1H), 1.41 (d, J=6.0 Hz, 6H, CH$_3$); $^{13}$C NMR (100.6 MHz, CDCl$_3$) δ 162.9, 157.4, 146.6, 144.5, 135.8, 135.7, 132.0, 131.0, 128.3, 125.2, 70.3, 21.8; LRMS Calcd. for $C_{15}H_{12}Cl_3NO_2$: 342.99. Found: 343 (M$^+$), 257 [(M$^+$-CO$_2$$_1$Pr)], 222, 186, 151.

Example 17

4,5-dichloro-6-(4-chlorophenyl)picolinic acid

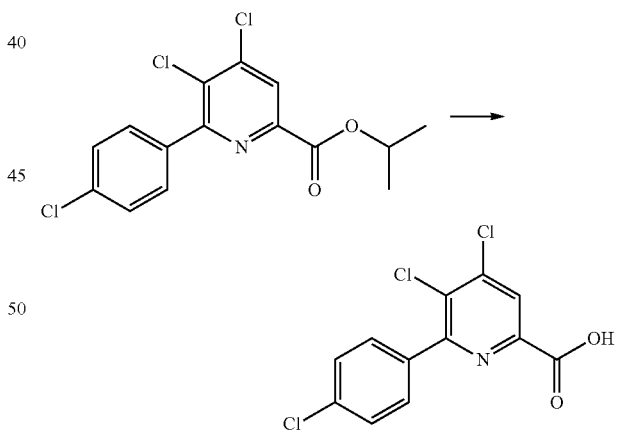

To a 125 mL 3-neck round bottom flask fitted with a condenser, nitrogen inlet, overhead stirring, thermometer and heating mantle was charged isopropyl 4,5-dichloro-6-(4-chlorophenyl) picolinate (7.6 g, 22.1 mmol) and isopropyl alcohol (70 mL). Reaction mixture was heated to 40° C. and potassium hydroxide (85%, 5.1 g, 77.4 mmol) and water (5 mL) were added. Solids precipitated from the mixture and it became difficult to stir. The mixture was diluted with water (250 mL) to dissolve most of the solids and allowed to stir at room temperature. Concentrated HCl (12 N, 5.6 mL) was added dropwise to the reaction mixture to achieve a pH of ~2 and solids precipitated from the mixture. The solids were isolated by vacuum filtration, washed with water (2×100 mL), and then dried to give 7.3 g (108% yield by weight) of 4,5-dichloro-6-(4-chlorophenyl)picolinic acid as a white solid. $^1$H NMR (400 MHz, THF/D$_2$O) δ 8.19 (d, J=11.2 Hz, 1H), 7.84-7.73 (m, 2H), 7.50 (dd, J=10.3, 3.5 Hz, 2H). $^{13}$C NMR (101 MHz, THF/D$_2$O) δ 167.70, 156.03, 152.40, 143.60, 136.49, 134.76, 131.22, 129.24, 128.04, 124.71, MP. 229° C.

Example 18

4,5-Dichloro-6-(4-chlorophenyl)picolinoyl chloride

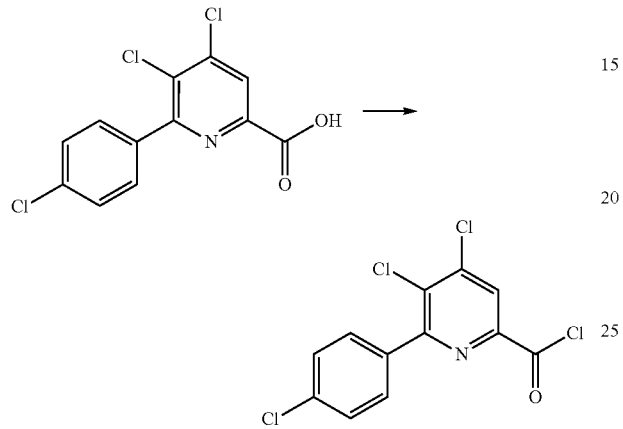

To a mixture of 4,5-dichloro-6-(4-chlorophenyl)picolinic acid (3.00 g, 9.9 mmol) in toluene (25 mL) was added thionyl chloride (1.08 mL, 14.9 mmol) and dimethylformamide (0.04 mL, 0.5 mmol). Reaction mixture was heated at 80° C. for 2.5 h. HPLC analysis of the reaction mixture treated with methanol and dimethylaminopyridine indicated starting material remaining. Reaction mixture was allowed to cool to room temperature and additional thionyl chloride (0.5 mL, 6.9 mmol) and dimethylformamide (0.04 mL, 0.5 mmol) were added. Reaction was heated at 80° C. for an additional 2 h. Reaction was allowed to cool to room temperature and concentrated under reduced pressure to provide a white solid. Toluene (40 mL) was added to dissolve the solid and concentrated under reduced pressure and then this process was performed a second time. 4,5-Dichloro-6-(4-chlorophenyl)picolinoyl chloride was isolated as a white solid (3.05 g, 96% yield). $^1$H NMR (400 MHz, CDCl$_3$) δ 8.15 (s, 1H), 7.79-7.72 (m, 2H), 7.53-7.46 (m, 2H). $^{13}$C NMR (101 MHz, CDCl$_3$) δ 168.66, 157.63, 146.48, 145.44, 136.35, 135.10, 134.28, 131.04, 128.63, 124.90. LRMS: Calcd. for C$_{12}$H$_8$Cl$_4$NO, 320.91. Found: m/z=257 (M$^+$-COCl), 222, 207, 186, 151.

Example 19

4,5-Dichloro-6-(4-chloro-2-fluoro-3-methyoxyphenyl)picolinoyl chloride

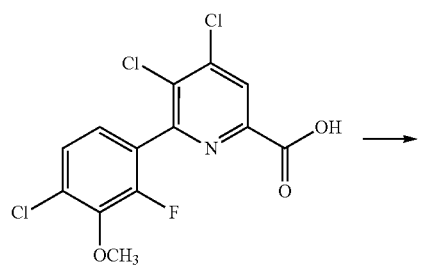

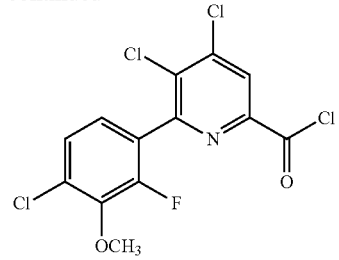

A mixture of 33.5 g (95 mmol) of 6-(4-chloro-2-fluoro-3-methoxyphenyl)-4,5-dichloro-2-pyridinecarboxylic acid, 10.2 mL (140 mmol) of thionyl chloride, 0.1 mL of N,N-dimethylforamide (DMF) and 200 mL of toluene was heated at 75° C. for 5 h. The reaction progress was monitored by conversion of the acid chloride to its methyl ester (one drop of reaction mixture added to 5 drops of a 10% wt methanol solution containing 4-(dimethylamino)pyridine, briefly heating to reflux, dilution with acetonitrile and injection). LC analysis indicated 8 area % remaining carboxylic acid and 3 area % of an unidentified closely following product. Another 5 mL of thionyl chloride and 0.1 mL of DMF was added, and heating was continued for an additional 2 h. After stirring at room temperature overnight, the reaction mixture was filtered to remove a small amount of an insoluble material. The filtrate was concentrated in vacuo, and toluene added twice and re-concentrated in vacuo to remove residual thionyl chloride. The white solid obtained (38.6 g) was dried in a vacuum oven at 40° C. to give 33.3 g of a white solid, mp 134-136° C. LC internal standard analysis (conversion to its methyl ester as described above) indicated 98.1 wt %. EIMS m/e (relative intensity) 369 (4Cl, 80), 332 (3Cl, 38), 304 (3Cl, 82), 269 (2Cl, 100), 254 (2Cl, 30), 226 (2Cl, 73), 191 (30), 156 (46); $^1$H NMR (400 MHz, CDCl$_3$) δ 8.23 (s, 1 H), 7.32 (dd, J=8, 2 Hz, 1 H), 7.15 (dd, J=8, 7 Hz, 1 H), 4.02 (dd, J=1 Hz, 3 H); $^{19}$F NMR (376 MHz, $^1$H decoupled, CDCl$_3$) δ 126.83.

The embodiments described above are intended merely to be exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A process for the preparation of a compound of the Formula I:

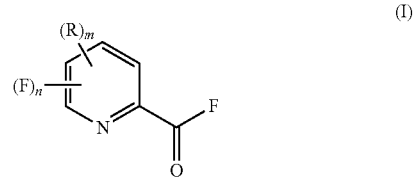

wherein
R is selected from the group consisting of halo; alkyl; cycloalkyl; alkenyl; alkynyl; alkoxy and aryl substituted with from 0 to 5 substituents independently selected from the group consisting of halo, C$_1$-C$_4$ alkyl, C$_1$-C$_4$ haloalkyl, C$_1$-C$_4$ alkoxy and C$_1$-C$_4$ haloalkoxy;
m is 0, 1, 2 or 3; and
n is 1, 2, 3 or 4;

wherein the sum of m and n is less than or equal to 4;
which comprises fluorinating a compound of Formula A:

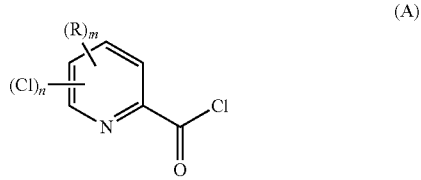

wherein R, m and n are as previously defined;
with a source of fluoride ion to produce the compound of the Formula I.

2. The process of claim 1, wherein m is 0.
3. The process of claim 1, wherein n is 2 or 3.
4. The process of claim 1, wherein the compound of Formula I is:

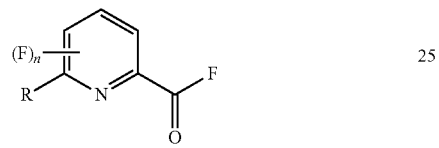

wherein R is aryl substituted with from 0 to 5 substituents independently selected from the group consisting of halo, $C_1$-$C_4$ alkyl, $C_1$-$C_4$ haloalkyl, $C_1$-$C_4$ alkoxy and $C_1$-$C_4$ haloalkoxy; and
n is 1, 2 or 3.

5. The process of claim 4, wherein n is 2.
6. The process of claim 1, wherein the compound of Formula I is:

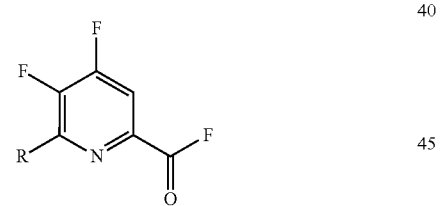

wherein R is phenyl substituted with from 0 to 5 substituents independently selected from the group consisting of halo, $C_1$-$C_4$ alkyl, $C_1$-$C_4$ haloalkyl, $C_1$-$C_4$ alkoxy and $C_1$-$C_4$ haloalkoxy.

7. The process of claim 1, wherein fluorinating a compound of Formula A is performed in the presence of a catalyst, wherein the catalyst is selected from the group consisting of a crown ether, a phosphonium halide, a polyether, a phosphazenium salt, and a tetra-substituted ammonium halide.

8. The process of claim 7, wherein the catalyst is a crown ether.

9. The process of claim 8, wherein the crown ether is 18-crown-6.

10. The process of claim 1, wherein the source of fluoride ion is a metal fluoride.

11. The process of claim 10, wherein the metal fluoride is selected from the group consisting of sodium fluoride, potassium fluoride and cesium fluoride.

12. The process of claim 11, wherein the metal fluoride is potassium fluoride.

13. The process of claim 1, which includes a solvent, wherein the solvent is an alkyl nitrile or an alkyl sulfone.

14. The process of claim 13, wherein the solvent is acetonitrile or sulfolane.

15. The process of claim 1 for the preparation of a compound of the formula

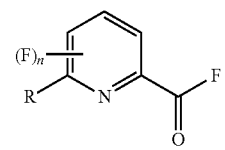

wherein
R is fluoro or phenyl substituted with from 0 to 5 substituents independently selected from the group consisting of halo, $C_1$-$C_4$ alkyl, $C_1$-$C_4$ haloalkyl, $C_1$-$C_4$ alkoxy and $C_1$-$C_4$ haloalkoxy; and
n is 1 or 2;
which comprises reacting a compound of Formula A:

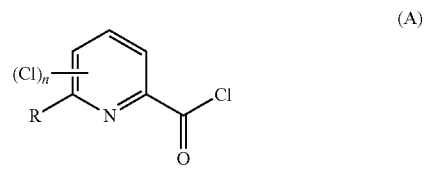

wherein R and n are as previously defined;
with potassium fluoride in the presence of a crown ether and a solvent.

16. The process of claim 15, wherein the solvent is acetonitrile or sulfolane.

17. A compound of the Formula I:

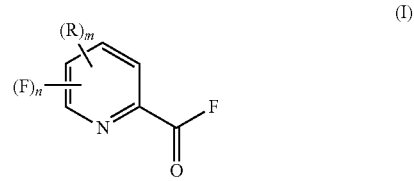

wherein
R is selected from the group consisting of halo; alkyl; cycloalkyl; alkenyl; alkynyl; alkoxy and aryl substituted with from 0 to 5 substituents independently selected from the group consisting of halo, $C_1$-$C_4$ alkyl, $C_1$-$C_4$ haloalkyl, $C_1$-$C_4$ alkoxy and $C_1$-$C_4$ haloalkoxy;
m is 0, 1, 2 or 3; and
n is 0, 1, 2, 3 or 4;
wherein the sum of m and n is between 1 and 4.

18. The compound of claim 17, wherein m is 0 and n is 1, 2, 3 or 4.

19. The compound of claim 17 of the formula:
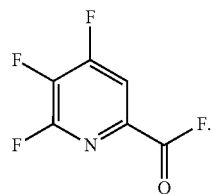
20. The compound of claim 17 of the formula:
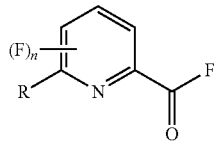
wherein R is aryl substituted with from 0 to 5 substituents independently selected from the group consisting of halogen, $C_1$-$C_4$ alkyl, $C_1$-$C_4$ haloalkyl, $C_1$-$C_4$ alkoxy and $C_1$-$C_4$ haloalkoxy; and
n is 1, 2 or 3.
21. The compound of claim 17, wherein n is 1 or 2.
22. The compound of claim 17 of the formula:
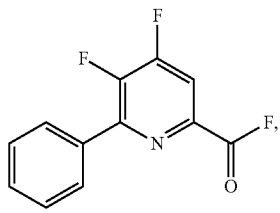
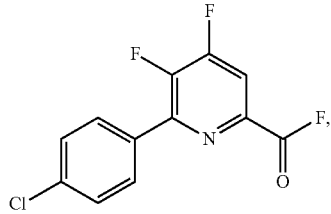
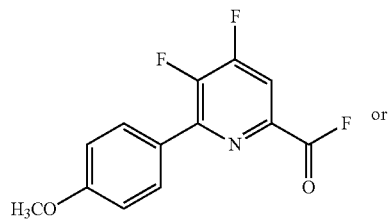
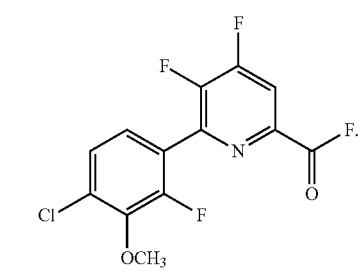
* * * * *